US012599558B2

(12) United States Patent (10) Patent No.: US 12,599,558 B2
Babiychuk et al. (45) Date of Patent: Apr. 14, 2026

(54) TAILORED LIPOSOMES FOR THE TREATMENT OF BACTERIAL INFECTIONS

(71) Applicant: UNIVERSITAET BERN, Bern (CH)

(72) Inventors: Eduard Babiychuk, Bern (CH); Annette Draeger, Bern (CH)

(73) Assignee: UNIVERSITAET BERN, Bern (CH)

( * ) Notice: Subject to any disclaimer, the term of this patent is extended or adjusted under 35 U.S.C. 154(b) by 461 days.

(21) Appl. No.: 17/957,402

(22) Filed: Sep. 30, 2022

(65) Prior Publication Data

US 2023/0031648 A1 Feb. 2, 2023

Related U.S. Application Data

(60) Division of application No. 17/537,862, filed on Nov. 30, 2021, now abandoned, which is a continuation of application No. 16/924,539, filed on Jul. 9, 2020, now abandoned, which is a division of application No. 14/404,985, filed as application No. PCT/EP2013/062207 on Jun. 13, 2013, now Pat. No. 10,744,089.

(30) Foreign Application Priority Data

Jun. 14, 2012 (EP) ..................................... 12171924
Jan. 29, 2013 (EP) ..................................... 13153039

(51) Int. Cl.
| | |
|---|---|
| *A61K 9/127* | (2025.01) |
| *A61K 9/10* | (2006.01) |
| *A61K 9/1271* | (2025.01) |
| *A61K 31/575* | (2006.01) |
| *A61K 31/688* | (2006.01) |

(52) U.S. Cl.
CPC ................ *A61K 9/127* (2013.01); *A61K 9/10* (2013.01); *A61K 9/1271* (2013.01); *A61K 31/575* (2013.01); *A61K 31/688* (2013.01)

(58) Field of Classification Search
CPC ........ A61K 9/127; A61K 9/10; A61K 9/1271; A61K 31/575; A61K 31/688
See application file for complete search history.

(56) References Cited

U.S. PATENT DOCUMENTS

| | | | |
|---|---|---|---|
| 3,641,247 A | 2/1972 | Cook | |
| 5,543,152 A | 8/1996 | Webb et al. | |
| 5,741,516 A * | 4/1998 | Webb ................... | A61K 9/1272 |
| | | | 514/283 |
| 8,906,855 B2 | 12/2014 | Simpkins | |
| 9,439,855 B2 | 9/2016 | Simpkins | |
| 9,782,349 B2 | 10/2017 | Hong et al. | |
| 10,716,756 B2 | 7/2020 | Simpkins | |
| 10,744,089 B2 | 8/2020 | Babiychuk et al. | |
| 2003/0175334 A1 | 9/2003 | Bolton et al. | |
| 2003/0236265 A1 | 12/2003 | Sayada | |

| | | | |
|---|---|---|---|
| 2006/0198882 A1 | 9/2006 | Barenholz et al. | |
| 2007/0122466 A1 | 5/2007 | Chancellor et al. | |
| 2009/0087482 A1 | 4/2009 | Needham | |
| 2009/0087842 A1 | 4/2009 | Ohtsuka et al. | |
| 2009/0186073 A1 | 7/2009 | Yamazaki et al. | |
| 2010/0151002 A1 | 6/2010 | Ahmad et al. | |
| 2011/0002982 A1 | 1/2011 | Tardi et al. | |
| 2013/0164370 A1 * | 6/2013 | Pumeranz .............. | C07K 9/008 |
| | | | 514/2.3 |
| 2013/0216606 A1 | 8/2013 | Venkatraman et al. | |
| 2015/0182460 A1 | 7/2015 | Hong et al. | |
| 2020/0230055 A1 | 7/2020 | Azeredo Da Silveira Lajaunias et al. | |
| 2021/0030677 A1 | 2/2021 | Azeredo Da Silveira Lajaunias et al. | |

FOREIGN PATENT DOCUMENTS

| | | | | |
|---|---|---|---|---|
| CN | 101623262 A | 1/2010 | | |
| CN | 102327220 A | 1/2012 | | |
| RU | 2424792 C2 | 7/2011 | | |
| WO | 9104019 A1 | 4/1991 | | |
| WO | WO-199104019 A1 * | 4/1991 | .............. | A61K 9/50 |
| WO | 9304672 A1 | 3/1993 | | |
| WO | WO-2006052767 A2 * | 5/2006 | ............. | A61K 31/47 |

(Continued)

OTHER PUBLICATIONS

Nisini, R. et al. "The multirole of liposomes in therapy and prevention of infectious diseases" (2018) Frontiers in Immunology 9, 155. (Year: 2018).*
Bergers, J.J. et al. "Liposomes as delivery systems in the prevention and treatment of infectious diseases" (1995) Pharm World Sci: 17(1): 1-11. (Year: 1995).*
U.S. Appl. No. 17/537,862, filed Nov. 30, 2021.
Wenjun Z. Martini, et al.; "Comparisons of normal saline and lactated Ringer's resuscitation on hemodynamics, metabolic responses, and coagulation in pigs after severe hemorrhagic shock"; Scaninavian Journal of Trauma, Resuscitation and Emergency Medicine; 2013; pp. 1-12.

(Continued)

*Primary Examiner* — Frederick F Krass
*Assistant Examiner* — Toriana N. Vigil
(74) *Attorney, Agent, or Firm* — BakerHostetler

(57) ABSTRACT

The invention relates to the use of empty liposomes of defined lipid composition or mixtures of empty liposomes of defined lipid composition and to the use of other lipid bilayers or monolayers of defined lipid composition for the treatment and prevention of bacterial infections. It has been found that such liposomes, in particular a two- and a four-component mixture of liposomes comprising cholesterol and sphingomyelin, liposomes consisting of sphingomyelin, liposomes comprising sphingomyelin and phosphatidylcholine, and liposomes comprising cholesterol and phosphatidylcholine efficiently sequestrate a variety of toxins secreted by bacteria, thus preventing binding of bacterial toxins to target cells and toxin-induced lysis of the target cells. Injected intravenously, liposome mixtures prevented death of laboratory mice infected with lethal doses of *Staphylococcus aureus* or *Streptococcus pneumoniae*.

12 Claims, 10 Drawing Sheets

(56)  References Cited

FOREIGN PATENT DOCUMENTS

| WO | 2008039989 A2 | 4/2008 |
| WO | 2013/186286 A1 | 12/2013 |
| WO | 2017/222912 A1 | 12/2017 |

OTHER PUBLICATIONS

Javier A. Neyra, MD.; "Association of Hyperchloremia with Hospital Mortality in Critically Ill Septic Patients"; Author Manuscript; Sep. 2015; pp. 1-14.

Bakker-Woudenberg et al., "Improved Efficacy of Ciprofloxacin Administered in Polyethylene Glycol-Coated Liposomes for Treatment of Klebsiella pneumoniae Pneumonia in Rats", Antimicrobial Agents and Chemotherapy, 2001, vol. 45, No. 5, pp. 1487-1492, 6 pages.

Cruse et al., "Human Lung Mast Cells Mediate Pneumococcal Cell Death in Response to Activation by Pneumolysin", J. Immunol, 2010, vol. 184, pp. 7108-7115, 9 pages.

J. Immunol, 2010, vol. 184, pp. 7108-7115, 9 pages.

Gonzalez et al., "Bacterial pore-forming toxins: The (w)hole story", Cell Mol Life Sci., 2008, vol. 65, pp. 493-507, 15 pages.

Klose et al., "Yeast Lipids Can Phase-separate into Micrometer-scale Membrane Domains", J. Biol. Chem., 2010, vol. 285, No. 39, pp. 30224-30232, 9 pages.

Monastyrskaya et al., "Annexins as intracellular calcium sensors", Cell Calcium, 2007, vol. 41, pp. 207-219, 13 pages.

International Search Report issued Aug. 2, 2013 in International (PCT) Application No. PCT/EP2013/062207.

Simons et al., "Revitalizing membrane rafts: new tools and insights", Nature Reviews, vol. 11, 2010, pp. 688-699.

Melyantseva Larisa Petrovna, "Antibacterial Action Of Liposomes And The Possibility Of Their Application For Prevention Of Injury Infection", RSFSR State Committee Of Santiary And Edidemiological Surveillance, Moscow Research Institute Of Epidemiology And Microbiology Named G.N. Gabrichevy, Moscow, 1992, with English Translation, 12 pages.

Taran Tatyana Viktoronva, "Biotechnology Of Producing Medicinal And Immunogenic Liposomal Compositions Used In The Treatment Of Experimental Hazardous Infections And Obtaining Raw Materials For Medical Medicine", Ministry Of Health And Social Development Of The Russian Federation Stavropol Scientific Research Animal Institute, Stavropol, 2004, with English Translation, 29 pages.

Campanha et al., "Interactions between cationic liposomes and bacteria: the physical-chemistry of the bactericidal action", Journal of Lipid Research, 1999, vol. 40, pp. 1495-1500.

Rosado et al., "The MACPF/CDC family of pore-forming toxins", Cellular Microbiology, 2008, vol. 10, No. 9, pp. 1765-1774.

Los et al., "Role of Pore-Forming Toxins in Bacterial Infectious Diseases", Microbiology and Molecular Biology Reviews, 2013, vol. 77, No. 2, pp. 173-207.

Simons et al., Revitalizing membrane rafts: new tools and insights, Nat. Rev. Mol., Cell Biol., 2010, 11, 688-699.

Azeredo Da Silveira et al., "Liposomes as novel anti-infectives targeting bacterial virulence factors?", Expert Review of Anti-Infective Therapy, 2015, vol. 13, No. 5, pp. 531-533.

Braun et al., "Pneumolysin, a Protein Toxin of Streptococcus pneumoniae, Induces Nitric Oxide Production from Macrophages", Nfection and Immunity, vol. 67, No. 8, Aug. 1999, pp. 3750-3756.

Cai et al., "Novel Insights for Systemic Inflammation in Sepsis and Hemorrhage", Mediators of Inflammation, vol. 2010, Article ID 642462, Apr. 2010, pp. 1-10.

Francois et al., "CAL02: a liposomal adjunctive anti-toxin therapy in infections. A new therapeutic approach for severe community-acquired pneumonia", PowerPoint from the European Congress of Clinical Microbiology and Infectious Diseases, Apr. 22-25, 2017, pp. 1-18.

Hammond et al., "Balanced Crystalloids versus Saline in Critically Ill Adults—A Systematic Review with Meta-Analysis", NEJM Evid, vol. 1, No. 2, Jan. 18, 2022, pp. 1-12.

Henry et al., "Engineered liposomes sequester bacterial exotoxins and protect from severe invasive infections in mice," Nature Biotechnology, 2014, vol. 33, No. 1, pp. 81-88.

Laterre et al., "CAL02, a novel antitoxin liposomal agent, in severe pneumococcal pneumonia: a first-in-human, double-blind, placebo-controlled, randomized trial," Lancet Infect Dis, May 2019, vol. 19, pp. 620-630.

Lee et al., "The Hypotension Period after Initiation of Appropriate Antimicrobial Administration Is Crucial for Survival of Bacteremia Patients Initially Experiencing Severe Sepsis and Septic Shock", J. Clin. Med., Aug. 12, 2020, vol. 9, 2617-2629.

Qu et al., "Case report of rescue of a patient with COVID-19 and shock after holmium laser lithotripsy", Int J Urol Nurs., 2022, vol. 16, No. 03, pp. 245-251.

Tracey et al., "Anti-cachectin/TNF monoclonal antibodies prevent septic shock during lethal bacteraemia", Nature, vol. 330, No. 6149, Dec. 17, 1987, pp. 662-664.

Weinberg et al., "Interleukin-1 and tumour necrosis factor cause hypotension in the conscious rabbit", Clinical Science, Feb. 16, 1988, vol. 75, No. 3, pp. 251-255.

Xu et al., "Noma in a boy with septic shock: a case report", BMC Pediatrics, 2019, vol. 19, 200, pp. 1-5.

* cited by examiner

A

B

C

A

B

A

B

C

TAILORED LIPOSOMES FOR THE TREATMENT OF BACTERIAL INFECTIONS

CROSS-REFERENCE TO RELATED APPLICATION

This application is a divisional of U.S. application Ser. No. 17/537,862, filed Nov. 30, 2021, which is a continuation of U.S. application Ser. No. 16/924,539, filed Jul. 9, 2020, which is a divisional of U.S. application Ser. No. 14/404, 985, filed Dec. 2, 2014, which is a U.S. National Stage of PCT/EP2013/062207, filed Jun. 13, 2013, which claims priority to EP 13153039.6, filed Jan. 29, 2013 and EP 12171924.9, filed Jun. 14, 2012, the entirety of which are incorporated by reference herein.

FIELD OF THE INVENTION

The invention relates to the use of empty liposomes or liposome mixtures and to the use of other lipid bilayers or monolayers of defined lipid composition for the treatment and prevention of bacterial infections. Likewise the invention relates to a treatment of such bacterial infections comprising administering empty liposomes or liposome mixtures, alone or in combination with standard antibiotic treatment. Furthermore the invention relates to new liposome mixtures as such.

BACKGROUND OF THE INVENTION

Bacterial infections remain one of the major threats to human lives. As bacterial resistance to even the most potent antibiotics increases, so too must the efforts to identify novel anti-bacterial strategies. Among other virulence factors, many pathogenic bacteria secrete toxins that kill eukaryotic cells by disturbing their plasma membrane. Bacterial pore-forming toxins are active on the cell surface, causing pore formation and disruption of the plasma membrane followed by either lysis or apoptosis of host target cells, whereas bacterial phospholipases induce the death of host cells by enzymatic degradation of plasmalemmal phospholipids.

Bacterial membrane-destabilizing toxins, such as cholesterol-dependent cytolysins (CDCs: pneumolysin O, streptolysin O, tetanolysin), α-hemolysin or bacterial phospholipases (phospholipase C, sphingomyelinase) play a critical role in the establishment and progression of infectious diseases. Such diseases are pneumonia, a major cause of death among all age groups and the leading cause of death in children in low income countries; bacteremia, a severe complication of infections or surgery, which is characterized by high mortality due to sepsis and septic shock; and meningitis, a life-threatening disease, which also leads to serious long-term consequences such as deafness, epilepsy, hydrocephalus and cognitive deficits.

To target host cells bacterial membrane-destabilizing toxins either bind to individual membrane lipids (lipid head groups) or exploit the non-homogenous nature of the lipid bilayer of eukaryotic cells' plasma membrane, interacting with microdomains enriched in certain lipid species (Gonzales M. R. et al., Cell. Mol. Life Sci. 2008, 65:493-507). The non-homogenous distribution of lipids within the bilayer is not favored by in vivo conditions since transmembrane proteins and the presence of a multitude of individual lipid species with variable lengths and saturation status of their acyl chain oppose lipid de-mixing and thus the formation of stable lipid microdomains (Simons K. and Geri M. J., Nat. Rev. Mol. Cell Biol. 2010, 11:688-99). However, lipid de-mixing can be taken to its extremes in artificial protein-free liposomes, manufactured from a limited number of carefully selected lipid species, where extended, stable lipid microdomains can be created (Kiose C. et al., J. Biol. Chem. 2010, 285:30224-32). Moreover, artificial liposomes allow for much higher relative concentrations of a particular lipid than those ever likely to occur in vivo. Therefore, liposomes displaying stable lipid microdomains of defined biochemical properties and possessing high relative concentrations of particular lipids can be produced. Liposomes are currently used in the cosmetic and pharmaceutical industries as carriers for topical and systemic drug delivery and are considered to be non-toxic.

SUMMARY OF THE INVENTION

The Invention relates to the use of empty liposomes of defined lipid composition or mixtures of empty liposomes of defined lipid composition for the treatment and prevention of bacterial infections, in particular skin lesions, bacteremia, meningitis, respiratory tract infections, such as pneumonia, and abdominal infections, such as peritonitis.

The invention furthermore relates to lipid bilayers or lipid monolayers of defined lipid composition covering non-lipid surfaces, for use in the treatment and prevention of bacterial infections.

Likewise the invention relates to a treatment of such bacterial infections comprising administering to a patient in need thereof a therapeutically effective amount of empty liposomes of defined lipid composition or mixtures of empty liposomes of defined lipid composition, and to a method of prevention of such bacterial inventions in a subject at risk. Furthermore the invention relates to a treatment of bacterial infections comprising administering to a patient in need thereof a therapeutically effective amount of empty liposomes of defined lipid composition or mixtures of empty liposomes of defined lipid composition, before, after, together or in parallel with a standard antibiotic treatment of the bacterial infection.

Furthermore the invention relates to new mixtures of empty liposomes of defined lipid composition.

A-D) Liposomes (1:1 w/w mixtures) containing cholesterol in combination with PC (3). Sm (4) or PS (5) but not with PE (6) protected THP-1 cells from cholesterol-dependent cytolysins: pneumolysin O (A), streptolysin O (B), tetanolysin (C) as well as from phospholipase C (D).

E) Liposomes (1:1 w/w) containing cholesterol in combination with Sm (4) but not with PC (3), PS (5) or PE (6) protected THP-1 cells from α-hemolysin.

F) Liposomes without cholesterol (7-9) were ineffective.

c (r.u.)=number of cells, maintained in the presence of a toxin (1, 3-9) related to the number of cells maintained in the absence of a toxin (2), is given in relative units (r.u.). PLY=pneumolysin O; SLO=streptolysin O; TL=tetanolysin; PLC=phospholipase C; HML=α-hemolysin. 1=Control (no liposomes); 2=Control (no toxin), 3=Ch:PC (1:1 w/w) liposomes; 4=Ch:Sm (1:1 w/w) liposomes; 5=Ch:PS (1:1 w/w) liposomes; 6=Ch: PE (1:1 w/w) liposomes; 7=PC:Sm (1:1 w/w) liposomes; 8=Sm liposomes; 9=PC liposomes.

Ch=cholesterol; PC=phosphatidylcholine; PS=phosphatidylserine; Sm=sphingomyelin; PE=phosphatidylethanolamine.

Figure 2:
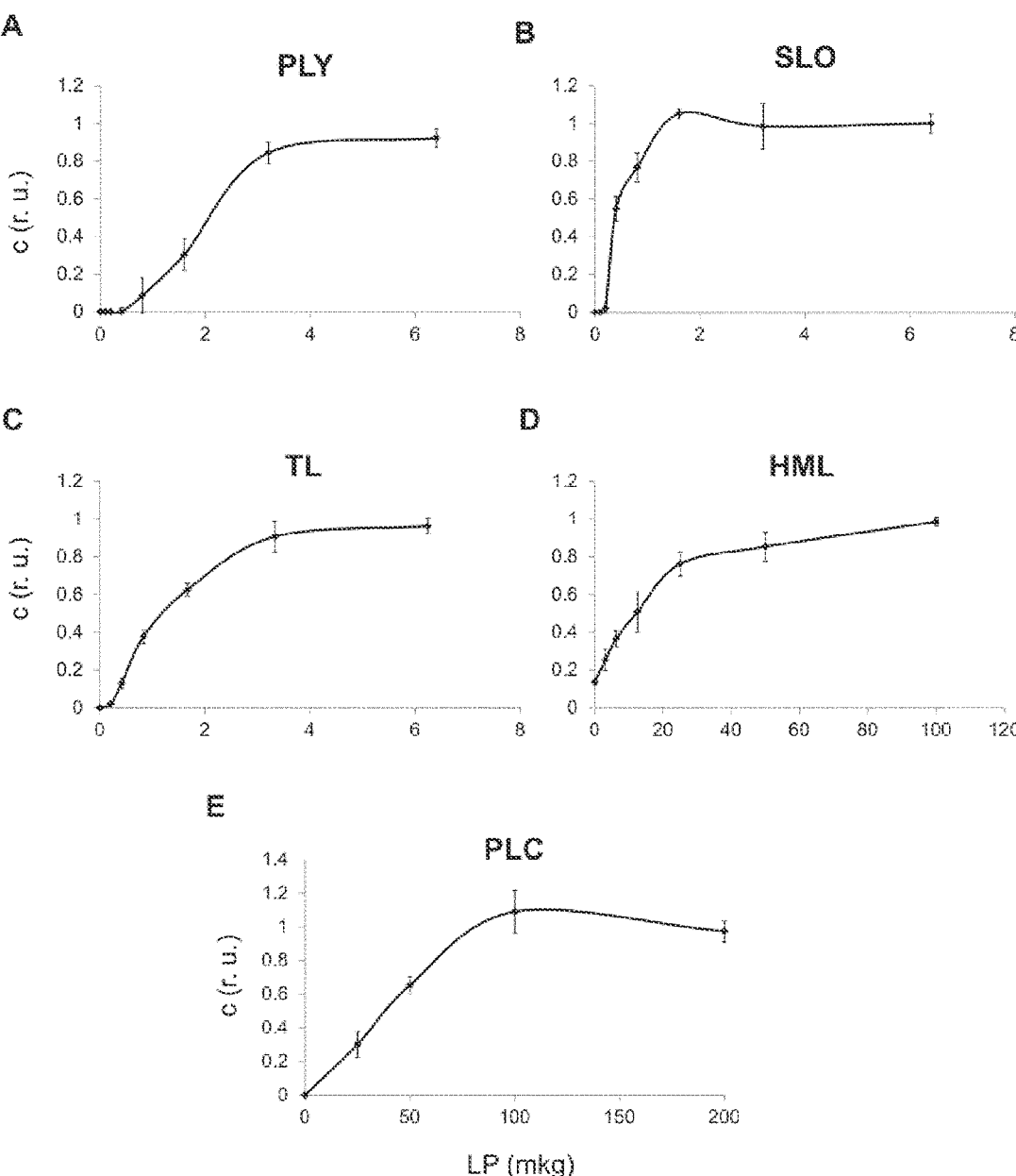

FIG. 2. Liposomes composed of cholesterol and sphingomyelin (1:1 w/w) protect monocytes from cholesterol-dependent cytolysins at microgram amounts, whereas 25-100 micrograms of the liposomes is required for protection against *Staphylococcus aureus* α-hemolysin and *Clostridium perfringens* phospholipase C.

A) Protection against 0.2 microgram of PLY. B) Protection against 0.4 microgram of SLO.

C) Protection against 0.2 microgram of TL. D) Protection against 1.2 microgram of HML.

E) Protection against 4.5 microgram of PLC.

c (r.u.)=number of cells, maintained in the presence of a toxin related to the number of cells maintained in the absence of a toxin, given in relative units. X-axis: LP (mkg)=amount of liposomes in micrograms. PLY=pneumolysin O; SLO=streptolysin O; TL=tetanolysin; HML=α-hemolysin; PLC=phospholipase C.

Figure 3:
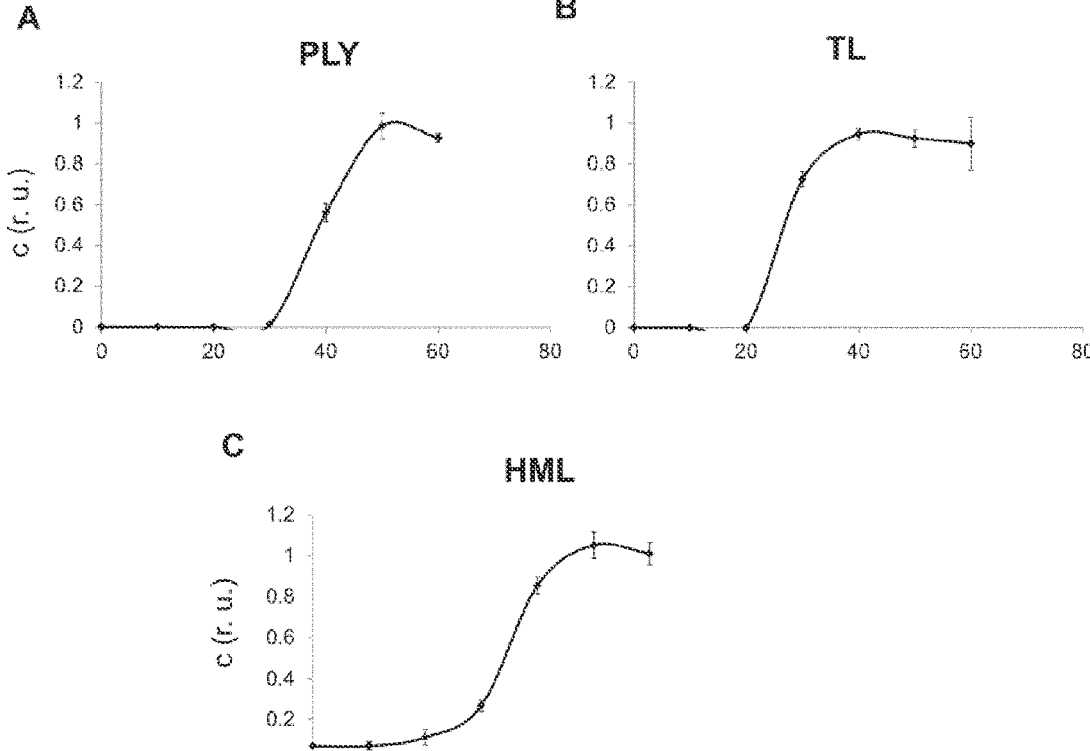

FIG. 3. Cholesterol in concentrations above 30% (w/w) is required for liposomes composed of cholesterol and sphingomyelin to protect monocytes from pneumolysin, tetanolysin or α-hemolysin.

A) Protection against 0.2 microgram of PLY. B) Protection against 0.2 microgram of TL.

C) Protection against 1.2 microgram of HML. c (r.u.)=number of cells, maintained in the presence of a toxin related to the number of cells maintained in the absence of a toxin, given in relative units. Ch (%)=percentage of cholesterol (w/w) in liposomes composed of cholesterol and sphingomyelin. PLY=pneumolysin; TL=tetanolysin; HML=α-hemolysin.

Figure 4:
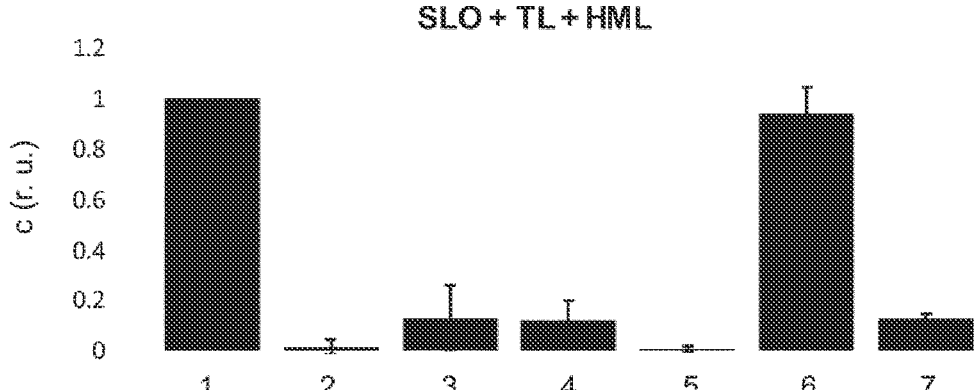
Figure 4:
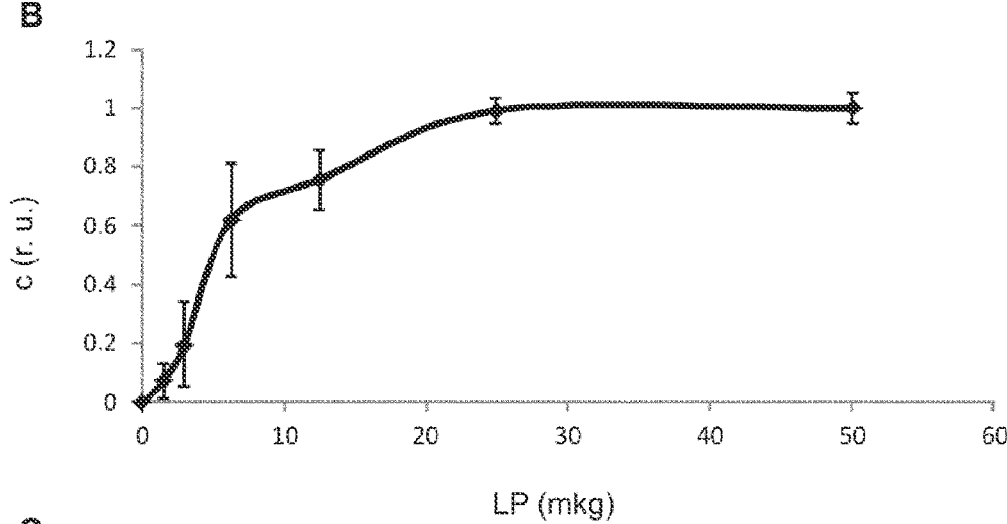
Figure 4:
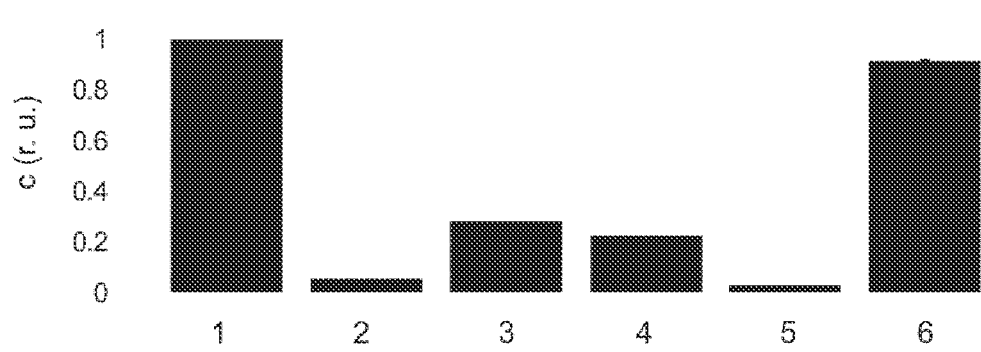

FIG. 4. Liposomes composed of cholesterol and sphingomyelin protect monocytes from a combination of cholesterol-dependent cytolysins and *S. aureus* α-hemolysin.

A) Ch:Sm (1:1 w/w) liposomes (6) exerted fully protective effects against the combined action of α-hemolysin (HML; 1.2 microgram), streptolysin O (SLO; 0.4 microgram) and tetanolysin (TL; 0.2 microgram), whereas Ch:PC (1:1 w/w) liposomes were ineffective (7). c (r.u.)=number of cells, maintained in the presence of toxins (2-7) related to the number of control cells maintained in the absence of toxins (1), in relative units. 1=Control (no toxins); 2=SLO, no liposomes; 3=TL, no liposomes; 4=HML, no liposomes; 5=SLO+TL+HML, no liposomes; 6=SLO+TL+HML, Ch:Sm liposomes; 7=SLO+TL+HML, Ch:PC liposomes. Ch=cholesterol; PC=phosphatidylcholine; Sm=sphingomyelin.

B) The full protective effect against the combined action of HML (1.2 microgram), SLO (0.4 microgram) and TL (0.2 microgram) was observed at 25 microgram of liposomes composed of Ch:Sm (1:1 w/w). LP (mkg)= amount of liposomes in micrograms.

C) Centrifugation experiments confirmed that all three toxins bind directly to Ch:Sm (1:1 w/w) liposomes. The toxins were pre-incubated with (6) or without (2-5) Ch:Sm liposomes. After centrifugation, the supernatants were added to the cells. 1=Control (no toxins); 2=SLO, no liposomes; 3=TL, no liposomes; 4=HML, no liposomes; 5=SLO+TL+HML, no liposomes; 6=SLO+TL+HML, Ch:Sm liposomes.

Figure 5:
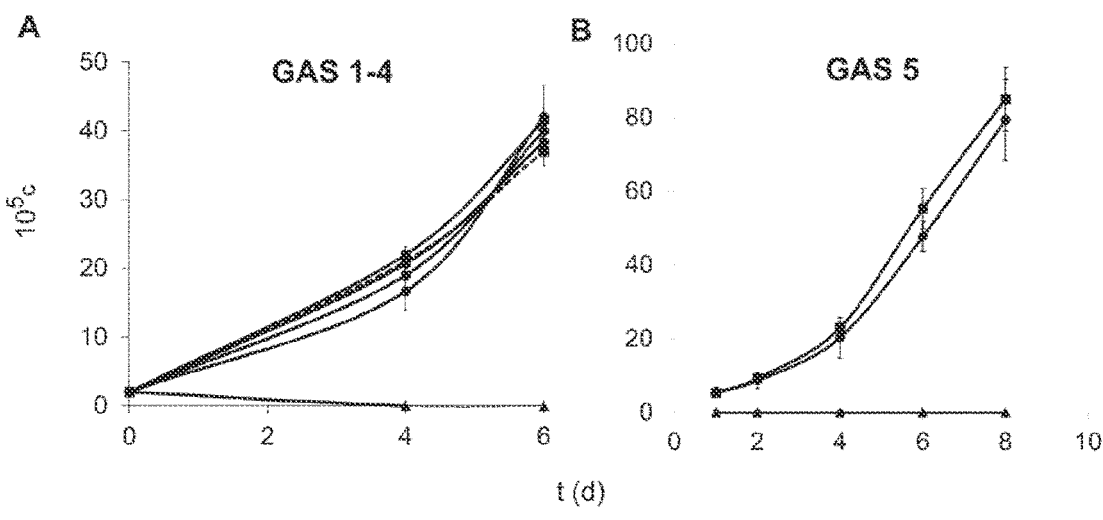
Figure 5:
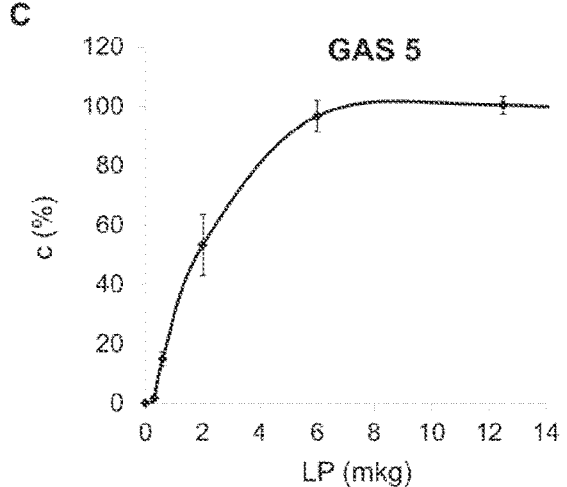

FIG. 5. Liposomes composed of cholesterol and sphingomyelin (1:1 w/w) protect monocytes from *Streptococcus pyogenes* toxins.

A,B) THP-1 cells proliferate in the presence of BHI broth (squares; dashed line in (A)). Culture supernatants of 5 *Streptococcus pyogenes* strains (GAS 1-5=clinical Isolates; all grown in BHI broth) effectively killed THP-1 cells (triangles), however the cells were protected from the effect of streptococcal toxins by liposomes composed of cholesterol and sphingomyelin (circles). $10^5$c=number of cells×$10^5$. t (d)=time after treatment (days).

C) Liposomes composed of cholesterol and sphingomyelin protect monocytes from culture supernatants of *Streptococcus pyogenes* in microgram amounts. c (%)=percentage of cells, maintained in the presence of bacterial supernatants related to cells maintained in the absence of the bacterial supernatants (100%). LP (mkg)= amount of liposomes in micrograms.

Figure 6:
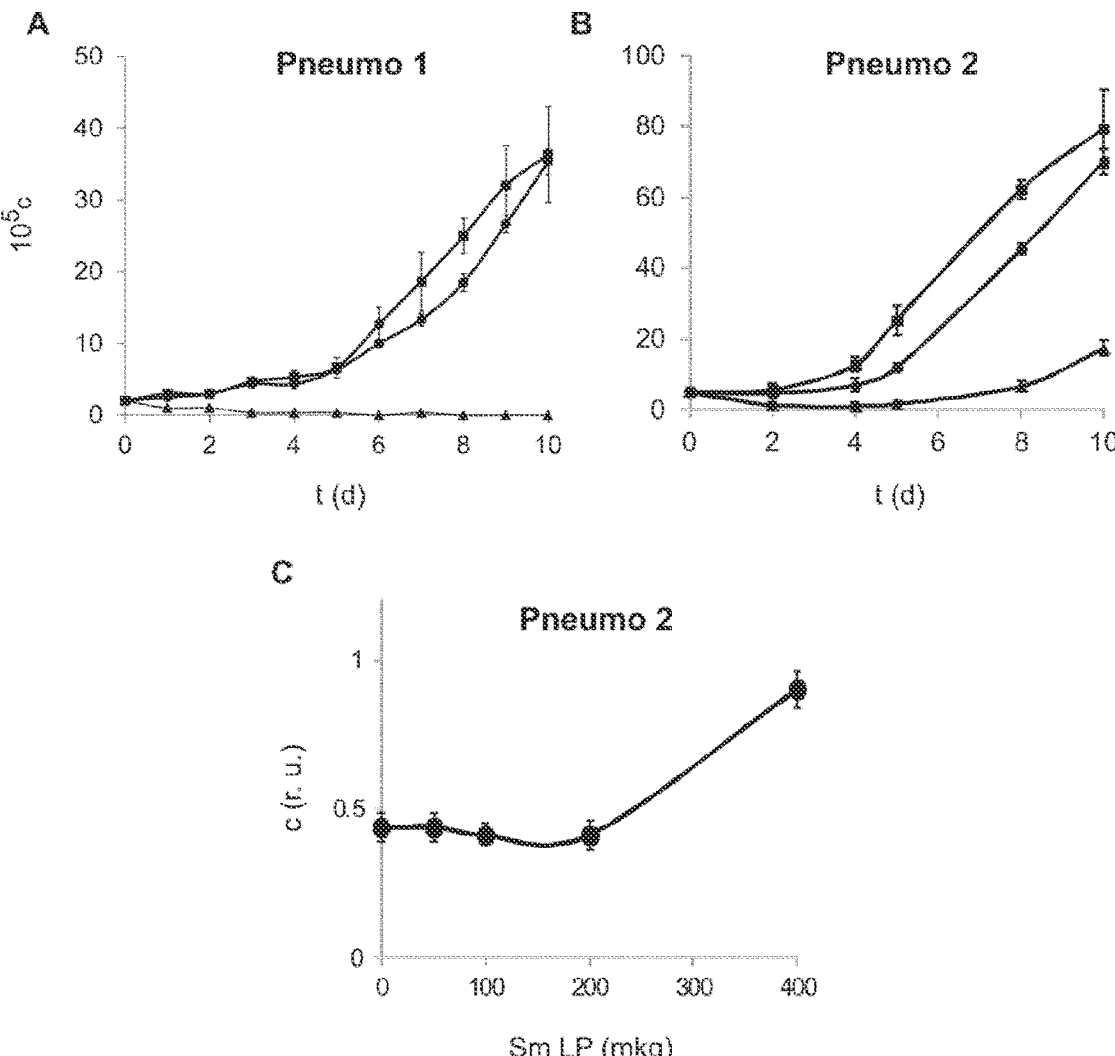

FIG. 6. Liposomes composed of cholesterol and sphingomyelin (1:1 w/w) in combination with sphingomyelin-only liposomes completely protect monocytes from *Streptococcus pneumoniae* toxins.

A,B) THP-1 cells proliferate in the presence of BHI broth (squares). Culture supernatants of 2 *Streptococcus pneumoniae* strains (Pneumo 1=clinical isolate and Pneumo 2=D39 strain; both grown in BHI broth) effectively killed THP-1 cells (triangles), however the cells were partially protected from the effect of *Streptococcus pneumoniae* toxins by liposomes composed of cholesterol and sphingomyelin (1:1 w/w) (circles). $10^5$c=number of cells×$10^5$. t (d)=time after treatment (days).

C) The mixture of cholesterol-containing and cholesterol-free, sphingomyelin-only liposomes was fully protective against *Streptococcus pneumoniae* toxins. The graph shows the protective effect of the liposomal mixtures composed of constant (400 µg) amount of cholesterol:sphingomyelin (1:1 w/w) liposomes and varying amounts (0-400 µg) of sphingomyelin-only liposomes.

c (r.u.)=number of cells, maintained in the presence of a bacterial supernatant related to the number of cells maintained in the absence of the supernatant, is given in relative units (r.u.). Sm LP (mkg)=amounts of sphingomyelin-only liposomes in micrograms.

Figure 7:
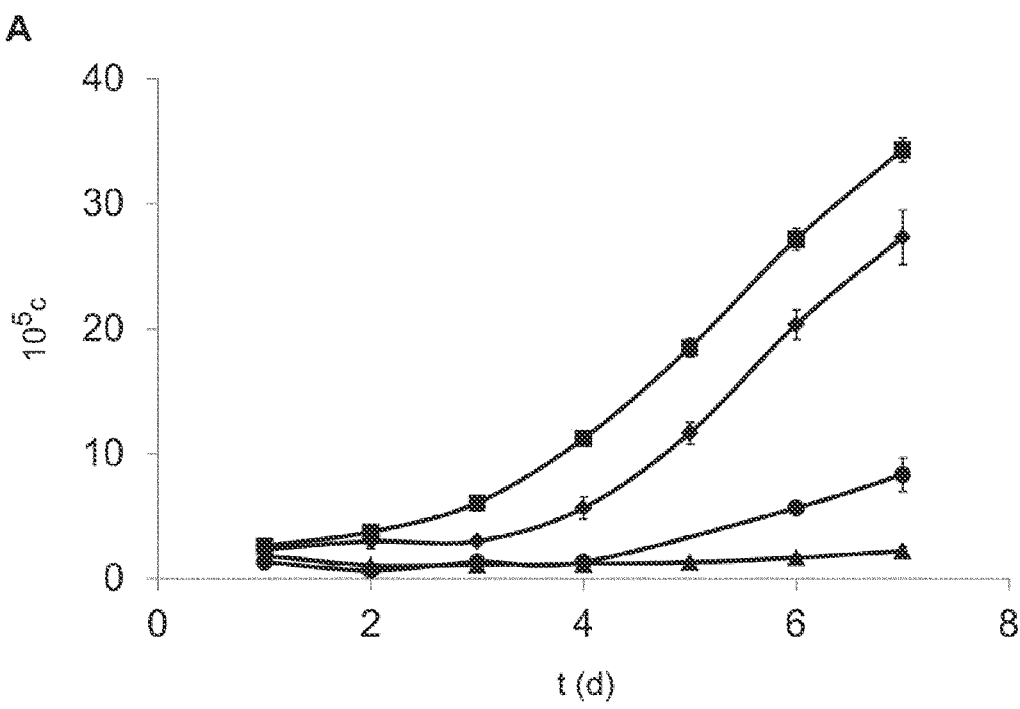
Figure 7:
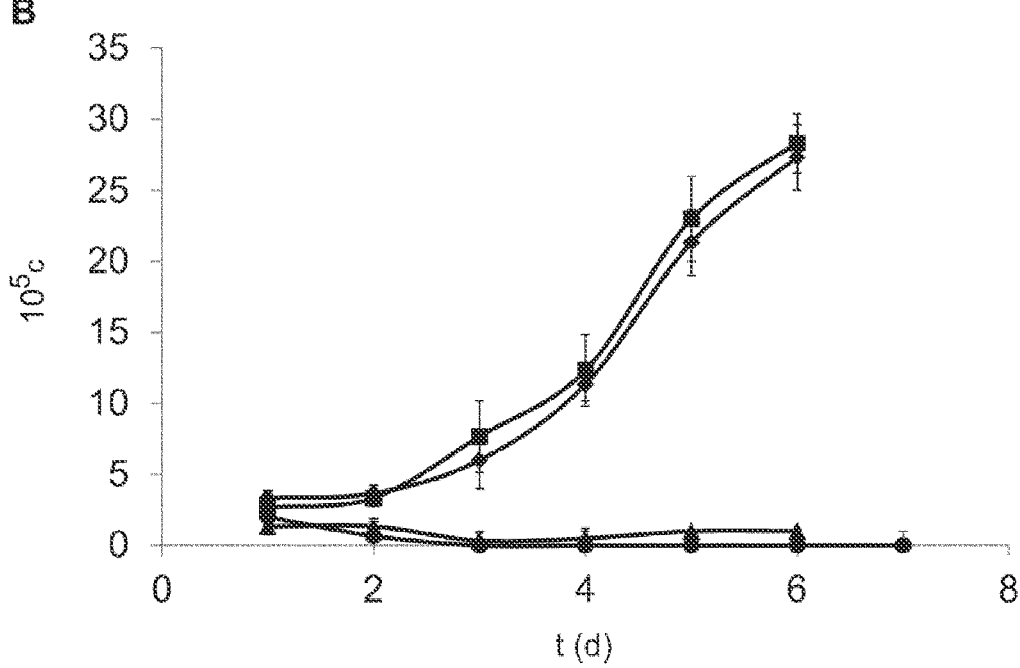

FIG. 7. Cholesterol:phosphatidylcholine liposomes (1:1 w/w) and a mixture of cholesterol:phosphatidylcholine (1:1 w/w) and sphingomyelin liposomes protect monocytes from toxins secreted by *Staphylococcus aureus* strain MRSA 2040.

THP-1 cells proliferate in the presence of BHI broth (squares). Culture supernatants of *Staphylococcus aureus* (grown in BHI broth) effectively kill THP-1 cells in the absence of liposomes (triangles). (A) 900 microgram (diamonds) of cholesterol:phosphatidylcholine (1:1 w/w) liposomes provide significant protection against bacterial toxins, whereas only limited protection was observed at 600 microgram (circles). (B) The full protection was observed for a mixture of 600 microgram of cholesterol:phosphatidylcholine (1:1 w/w) liposomes with 75 microgram of Sm liposomes (diamonds). 900 microgram of Sm liposomes used alone was ineffective (circles). $10^5$c=number of cells×$10^5$. t (d)=time after treatment (days).

Figure 8:
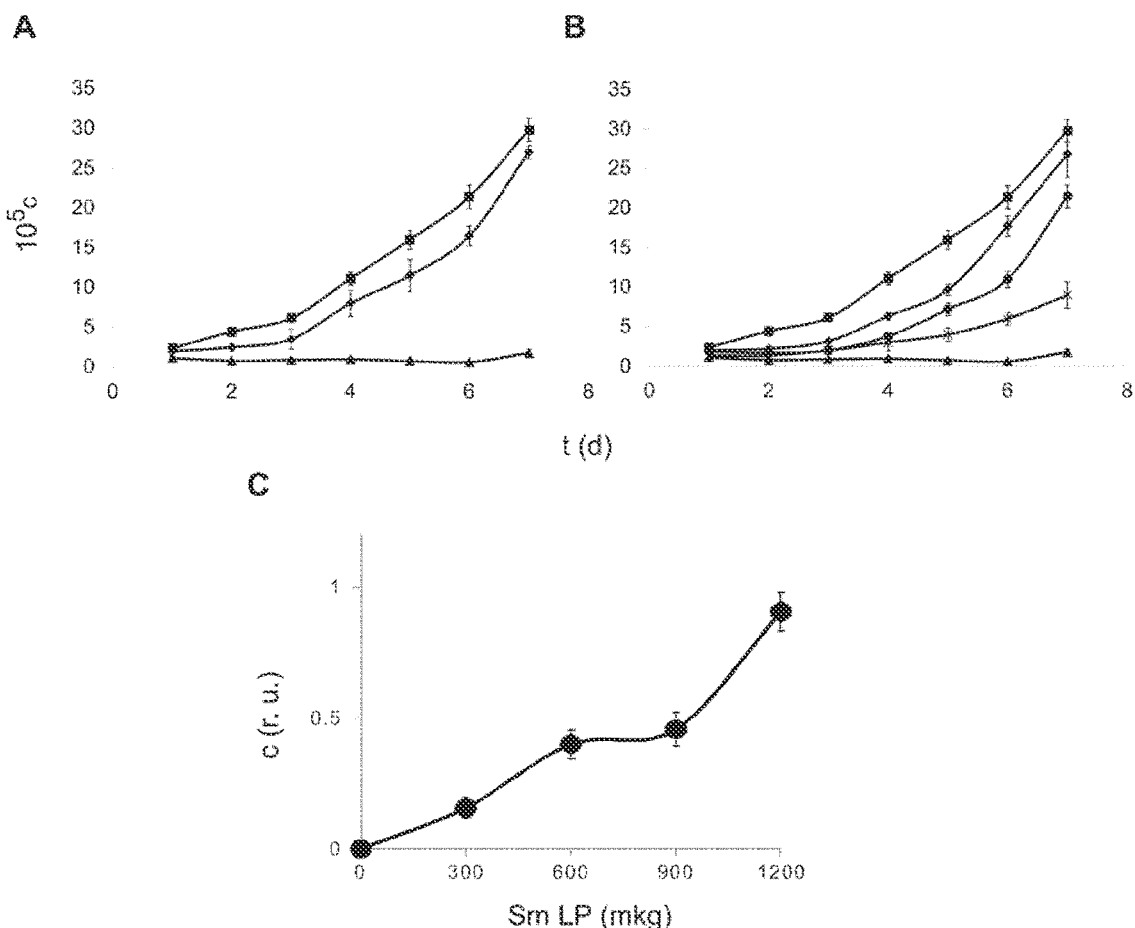

FIG. 8. Cholesterol-free, sphingomyelin-containing liposomes and a mixture of cholesterol:phosphatidylcholine (1:1 w/w) and sphingomyelin-only liposomes protect monocytes from toxins secreted by *Staphylococcus aureus* Doppelhof strain.

A,B) THP-1 cells proliferate in the presence of BHI broth (squares). Culture supernatants of *Staphylococcus aureus* (grown in BHI broth) effectively kill THP-1 cells in the absence of liposomes (triangles). (A) 1200 microgram (diamonds) of sphingomyelin liposomes provided significant protection against bacterial toxins. (B) When used at 600 microgram, the most potent protection was observed for a mixture of sphingomyelin and sphingomyelin:phosphatidylcholine (1:1 w/w) (diamonds), whereas sphingomyelin liposomes alone (circles) and sphingomyelin:phosphatidylcholine (1:1 w/w) liposomes alone (asterisks) were less effective. C) A mixture of cholesterol-containing and cholesterol-free, sphingomyelin-only liposomes was fully protective against toxins secreted by the *Staphylococcus aureus* Doppelhof strain. The graph shows the protective effect of the liposomal mixtures composed of constant (600 μg) amount of cholesterol:phosphatidylcholine (1:1 w/w) liposomes and varying amounts (0-1200 μg) of sphingomyelin-only liposomes.

$10^5$c=number of cells×$10^5$. t (d)=time after treatment (days). c (r.u.)=number of cells, maintained in the presence of a bacterial supernatant related to the number of cells maintained in the absence of the supernatant, is given in relative units (r.u.). Sm LP (mkg) =amounts of sphingomyelin-only liposomes in micrograms.

Figure 9:
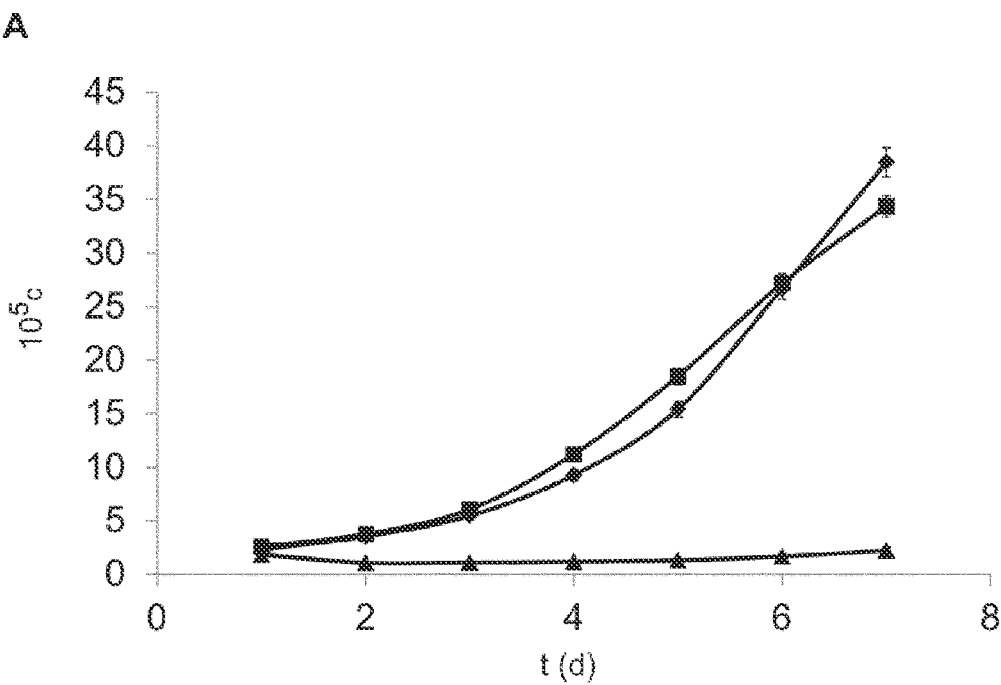
Figure 9:
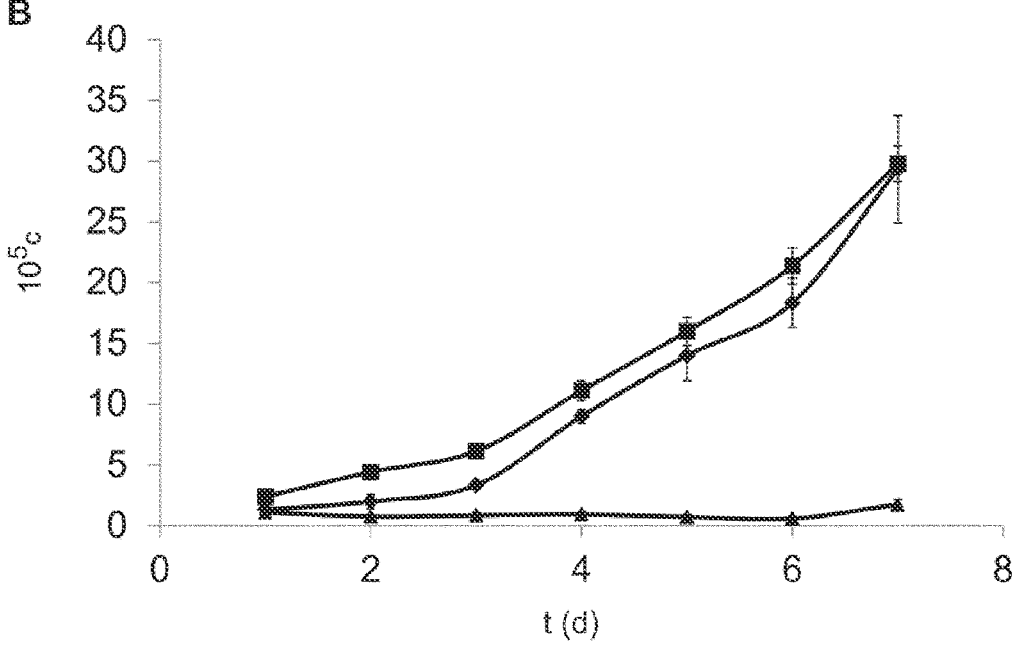

FIG. 9. A 4-component mixture of cholesterol:sphingomyelin (1:1 w/w), sphingomyelin-only, sphingomyelin:phosphatidylcholine (1:1 w/w) and cholesterol:phosphatidylcholine (1:1 w/w) liposomes protect monocytes from toxins secreted by both Doppelhof and MRSA 2040 strains of *Staphylococcus aureus*.

THP-1 cells proliferate in the presence of BHI broth (squares). Culture supernatants of MRSA 2040 (A) or Doppelhof (B) *Staphylococcus aureus* strains (grown in BHI broth) effectively kill THP-1 cells in the absence of liposomes (triangles), however the cells are completely protected from either MRSA 2040 (A) or Doppelhof (B) toxins by 1200 microgram of the 4-component liposomal mixture (1:1:1:1). $10^5$c=number of cells×$10^5$. t (d)=time after treatment (days).

Figure 10:
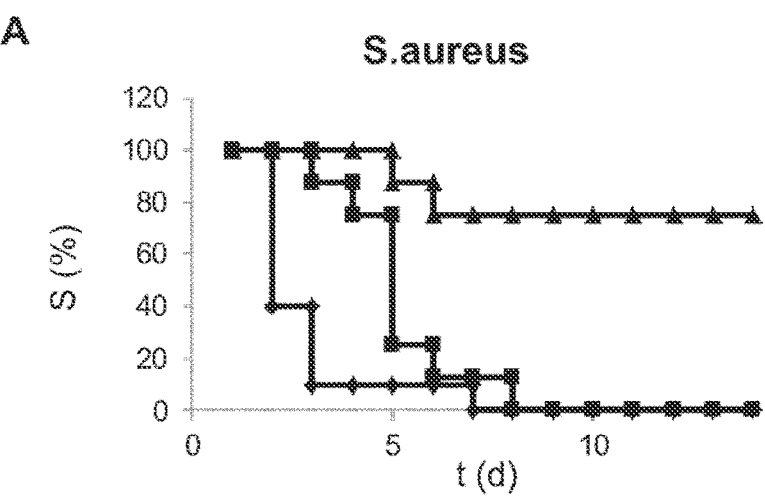
Figure 10:
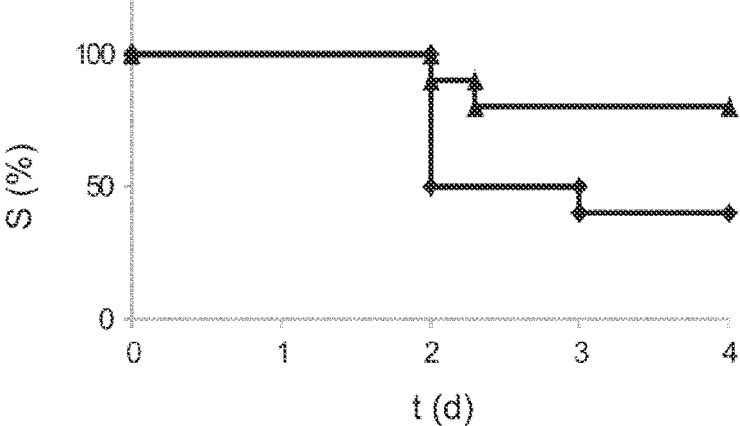
Figure 10:
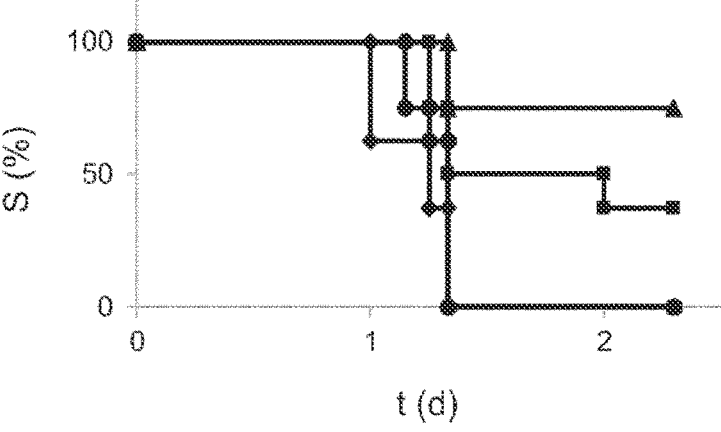

FIG. 10. Liposomes protect mice from *Staphylococcus aureus* bacteremia, from *Streptococcus pneumoniae* pneumonia and from *Streptococcus pneumoniae* bacteremia.

A) Laboratory mice were injected intravenously with a lethal dose of the Doppelhof *Staphylococcus aureus* strain. At 1, 5 and 24 hours after injection of bacteria, the mice were injected with either 25-50 microliter of normal saline (diamonds) or 25 microliter (1 mg) of cholesterol:sphingomyelin (1:1 w/w) liposomes (squares) or 50 microliter (2 mg) of a 1:2:2 mixture of cholesterol:sphingomyelin (1:1 w/w) liposomes+sphingomyelin-only liposomes+sphingomyelin:phosphatidylcholine (3:1 w/w) liposomes (triangles).

B) Mice were infected intranasally with the *Streptococcus pneumoniae* strain D39. 30 minutes following injection of bacteria, the mice received either an injection of 50 microliter of normal saline (diamonds) or a single intranasal injection of 50 microliter (2 mg) of a 1:1:1:1 mixture of cholesterol:sphingomyelin (1:1 w/w)+cholesterol:phosphatidylcholine (1:1 w/w)+sphingomyelin-only+sphingomyelin:phosphatidylcholine (3:1 w/w) liposomes (triangles).

C) Mice were injected intravenously with a lethal dose of the *S. pneumoniae* strain D39. At 8 and 12 hours following injection of bacteria, the mice received intravenously 75 microliter/injection (3 mg) of the following liposomes: 1) a 1:1 mixture of cholesterol:sphingomyelin (1:1 w/w)+sphingomyelin-only liposomes (triangles); 2) cholesterol:sphingomyelin (1:1 w/w) liposomes (squares); 3) sphingomyelin-only liposomes (circles) or 4) normal saline (diamonds).

S (%)=percent surviving mice. t (d)=time after infection (days)

DETAILED DESCRIPTION OF THE INVENTION

Engineered to possess higher than in vivo affinities for membrane-targeting toxins, inhaled or intravenously injected or infused empty liposomes and liposome mixtures serve as traps for bacterial toxins residing in blood or airways of infected patients, paving a way for a novel anti-bacterial toxin-sequestrating therapy.

The invention relates to the use of empty liposomes of defined lipid composition or mixtures of empty liposomes of defined lipid composition for the treatment and prevention of bacterial infections, in particular bacteremia, meningitis, bacterial skin infections, respiratory tract infections, such as pneumonia, and abdominal infections, such as peritonitis.

Liposomes of the invention are empty liposomes, i.e. liposomes not encapsulating any antibiotic or other drug. They may, if desired, be used in combination with known or novel liposomes carrying drugs.

The present study shows that artificial liposomes of precisely defined lipid composition or mixtures of liposomes of precisely defined lipid composition efficiently sequestrate purified pore-forming toxins and phospholipase C, thereby preventing their binding to the target cells. Consequently, the application of liposomes or their mixtures prevent the lysis of cultured epithelial cells and monocytes induced by the application of purified toxins or culture supernatants of *Streptococcus pneumonia*, *Streptococcus pyogenes* and *Staphylococcus aureus* and protect laboratory mice from death due to an experimentally induced bacteremia or pneumonia.

The invention relates to the use of empty liposomes of defined lipid composition or mixtures of empty liposomes of defined lipid composition for the treatment and prevention of bacterial Infections.

The invention furthermore relates to lipid bilayers or lipid monolayers of defined lipid composition covering non-lipid surfaces, for use in the treatment and prevention of bacterial infections. Non-lipid surfaces considered are, for example, medical appliances, biodegradable beads, and nanoparticles.

Liposomes considered are artificial liposomes of 20 nm to 10 μm, preferably 20 to 500 nm, comprising lipids or phospholipids selected from the group of sterols, sphingolipids and glycerolipids, in particular selected from the group consisting of cholesterol, sphingomyelins, ceramides, phosphatidylcholines, phosphatidylethanolamines, phosphatidylserines, diacylglycerols, and phosphatidic acids containing one (lyso-) or two (diacyl-), saturated or unsaturated fatty acids longer than 4 carbon atoms and up to 28 carbon atoms.

The composition of lipid bilayers or lipid monolayers considered is the same as indicated for liposomes.

Fatty acids comprising between 4 and 28 carbon atoms are, for example, saturated linear alkanecarboxylic acids, preferably with an even number of carbon atoms, such as between 12 and 26 carbon atoms, for example lauric, myristic, palmitic, stearic, arachidic, or behenic acid, or unsaturated linear alkanecarboxylic acids, preferably with an even number of between 12 and 26 carbon atoms and one, two or more, preferably up to six double bonds in trans or, preferably cis configuration, for example oleic acid, linoleic acid, alpha-linoleic acid, arachidonic acid, or erucic acid.

Empty liposomes means that the liposomes considered in the present invention do not incorporate antibiotic or other drugs. "Incorporated" as used herein means encapsulated into the cavity of the liposome, within the potential double layer of the liposome, or as part of the membrane layer of the liposome. Liposomes as used herein also exclude liposomes modified with binding agents such as antibodies and mono- or oligosaccharides, e.g. as in glycolipids. However, liposomes modified with polyethylene glycol (PEG) are considered as part of this invention. PEG is known to modify the circulation time of liposome.

In particular, the invention relates to the use of empty liposomes comprising cholesterol and sphingomyelin, and of mixtures of empty liposomes comprising cholesterol and sphingomyelin, or phosphatidylcholine and sphingomyelin, with other empty liposomes of defined lipid composition, such as liposomes comprising lipids or phospholipids selected from the group consisting of sterols, sphingolipids and glycerolipids, in particular selected from the group consisting of cholesterol, sphingomyelins, ceramides, phosphatidylcholines, phosphatidylethanolamines, phosphatidylserines, diacylglycerols, and phosphatidic acids containing one or two saturated or unsaturated fatty acids longer than 4 carbon atoms and up to 28 carbon atoms, for the treatment and prevention of bacterial infections.

In one embodiment, the invention relates to the use of empty liposomes comprising sphingomyelin and 30% (w/w) or more cholesterol, and of mixtures of empty liposomes comprising sphingomyelin and 30% (w/w) or more cholesterol with other empty liposomes as defined herein, for the treatment and prevention of bacterial infections. In particular, the invention relates to the use of empty liposomes consisting of sphingomyelin and of 30% (w/w) or more cholesterol, and of mixtures of empty liposomes consisting of sphingomyelin and of 30% (w/w) or more cholesterol with other empty liposomes as defined herein, for the treatment and prevention of bacterial infections. More particularly, the invention relates to the use of empty liposomes consisting of sphingomyelin and of between 35% and 65% (w/w) cholesterol, preferably between 40% and 60% 55% (w/w) cholesterol, in particular between 45% and 55% (w/w) cholesterol, such as around 50% (w/w) cholesterol, and of mixtures of empty liposomes consisting of sphingomyelin and of between 35% and 65%, or 40% and 60% 55%, or 45% and 55%, e.g. around 50% (w/w) cholesterol with other empty liposomes as defined herein, for the treatment and prevention of bacterial infections.

In a particular embodiment, the invention relates to the use of a liposome mixture of empty liposomes comprising or consisting of cholesterol and sphingomyelin, with other empty liposomes comprising or consisting of sphingomyelin, for the treatment and prevention of bacterial infections.

In another embodiment, the invention relates to the use of a liposome mixture of empty liposomes comprising or consisting of phosphatidylcholine and sphingomyelin with other empty liposomes as defined herein, for the treatment and prevention of bacterial infections. In particular, the invention relates to the use of a liposome mixture of empty liposomes comprising or consisting of phosphatidylcholine and sphingomyelin with other empty liposomes comprising or consisting of sphingomyelin, for the treatment and prevention of bacterial infections.

In a particular embodiment, the invention relates to the use of a three-component liposome mixture of empty liposomes comprising or consisting of cholesterol and sphingomyelin with other empty liposomes comprising or consisting of phosphatidylcholine and sphingomyelin, and with empty liposomes consisting of sphingomyelin, for the treatment and prevention of bacterial infections.

In yet another particular embodiment, the invention relates to the use of a four-component liposome mixture of empty liposomes comprising or consisting of cholesterol and sphingomyelin with other empty liposomes comprising or consisting of phosphatidylcholine and sphingomyelin, with empty liposomes consisting of sphingomyelin, and with empty liposomes comprising or consisting of cholesterol and phosphatidylcholine, for the treatment and prevention of bacterial infections.

The particular composition of lipid bilayers or lipid monolayers considered is the same as indicated for liposomes, preferably comprising cholesterol and sphingomyelin, and optionally phosphatidylcholine.

It is understood that the empty liposomes as defined above, the mixtures of empty liposomes as defined above, and the lipid bilayers or lipid monolayers may be used together with further compounds. For example, it is possible to add components to prepare standard pharmaceutical compositions. It is also considered to add drugs or drug-like compounds, or to add further liposomes incorporating drugs or drug-like compounds in the liposome interior.

Drugs considered are, in particular, antibiotics. Such antibiotics are, for example, carbapenems, such as imipenem/cilastatin, meropenem, ertapenem, and doripenem; $1^{st}$ generation cephalosporins, such as cefadroxil and cefalexin; $2^{nd}$ generation cephalosporins, such as cefuroxime, cefaclor, and cefprozil; $3^{rd}$ generation cephalosporins, such as ceftazidime, ceftriaxone, cefixime, cefdinir, cefditoren, cefotaxime, cefpodoxime, and ceftibuten. $4^{th}$ generation cephalosporins, such as cefepime; $5^{th}$ generation cephalosporins, such as ceftaroline fosamil and ceftobiprole; glycopeptides, such as vancomycin, teicoplanin, and telavancin; macrolides, such as clarithromycin, azithromycin, dirithromycin, erythromycin, roxithromycin, troleandomycin, telithromycin, spectinomycin, and spiramycin; penicillins, such as amoxicillin, flucloxacillin, oxacillin, carbenicllin, and piperacillin; penicillin combinations, such as amoxicillin/clavulanate, piperacillin/tazobactam, ampicillin/sulbactam, and ticarcillin/clavulanate; quinolones, such as ciprofloxacin (e.g. Aradigm's liposomal ciprofloxacin) and moxifloxacin; drugs against mycobacteria, such as rifampicin (rifampin in US), clofazimine, dapsone, capreomycin, cycloserine, ethambutol, ethionamide, isoniazid, pyrazinamide, rifabutin, rifapentine, and streptomycin; other antibiotics, such as metronidazole, arsphenamine, chloramphenicol, fosfomycin, fusidic acid, linezolid, mupirocin, platensimycin, quinupristin/dalfopristin, rifaximin, thiamphenicol, tigecycline, and tinidazole; aminoglycosides, such as amikacin, gentamicin, kanamycin, neomycin, netilmicin, tobramycin (e.g. Axentis' Fluidosomes™ tobramycin) and paromomycin; sulfonamides, such as mafenide, sulfonamidochrysoidine, sulfacetamide, sulfadiazine, silver sulfadiazine, sulfamethizole, sulfamethoxazole, sulfanilamide, sulfasalazine, sulfisoxazole, trimethoprim, and trimethoprim-sulfamethoxazole (co-trimoxazole, TMP-SMX); tetracyclines, such as demeclocycline, doxycycline, minocycline, oxytetracycline, and tetracycline; lincosamides, such as clindamycin, and lincomycin; and lipopeptides, such as daptomycin.

Further drugs considered are anti-cancer agents, for example vincristine sulfate, vincristine, cytarabine, daunorubicin, and doxorubicin.

Still other drugs considered are anti-inflammatory drugs, for example corticosteroids (glucocorticoids), such as hydrocortisone (cortisol), cortisone, prednisone, prednisolone, methylprednisolone, dexamethasone, betamethasone, triamcinolone, beclometasone, fludrocortisone acetate, deoxycorticosterone acetate (DOCA), aldosterone, budesonide, desonide, and fluocinonide; non-steroidal anti-inflammatory drugs, e.g. salicilates, such as aspirin (acetylsalicylic acid), diflunisal, and salsalate; propoinic acid derivatives, such as ibuprofen, dexibuprofen, naproxen, fenoprofen, ketoprofen, dexketoprofen, flurbiprofen, oxaprozin, and loxoprofen; acetic acid derivatives, such as indomethacin, tolmetin, sulindac, etodolac, ketorolac, diclofenac, and nabumetone; enolic acid (oxicam) derivatives, such as piroxicam, meloxicam, tenoxicam, droxicam, lornoxicam, and isoxicam; fenamic acid derivatives (fenamates), such as mefenamic acid, meclofenamic acid, flufenamic acid, and tolfenamic acid; selective COX-2 inhibitors (coxibs), such as Celecoxib; and others, such as licofelone.

Further drugs considered are vasopressors and vasoconstrictors, for example vasopressin, oxymetazoline, phenylephrine, propylhexedrine, pseudoephedrine, epinephrine, norepinephrine, dopamine, and antihistamines.

Also considered are other type of drugs, for example paracetamol (pain killer), amphotericin B (against fungal Infections), bupivacaine (post-surgical pain control), vaccines against hepatitis A, influenza, tetanus, evasive MRSA, pertussis, diphtheria, meningococcus, cholera, typhoid, anthrax, pneumococcus (e.g. Prevnar 13®), and other antibacterial vaccines, morphine (pain killer), verteporfin (ophthalmological diseases), estradiol (menopausal disturbances), Aganocide® compounds, e.g. auriclosene (NVC-422, N,N-dichloro-2,2-dimethyltaurine (anti-bacterials), M Bio Technology's liposome particles comprising specific lipid bacterial antigens, e.g. bacterium mimic particles as vaccines (*Mycoplasma* infections including pneumonia), and bacteriophages.

Further drugs considered are antitoxins, for example tetanus antitoxin, such as tetanus immunoglobulin, nanosponges, polymeric nanoparticles, biomimetic polymeric nanoparticle core surrounded by host cell membranes (such as red blood cell membranes), toxin-targeting monoclonal antibodies and antibody fragments, natural compounds Inhibiting specific toxin productions, Inhibitors of the bacterial toxin secretion system, such as T3SS inhibitors, toxin-binding mucin-type fusion proteins, soluble T cell receptors acting as decoy to neutralize toxins, and peptides that inhibit the processing of toxins.

Furthermore the invention relates to new mixtures of empty liposomes of defined lipid composition. In particular, the invention relates to mixtures of empty liposomes comprising cholesterol and sphingomyelin, or phosphatidylcholine and sphingomyelin, with other empty liposomes of defined lipid composition, such as liposomes comprising lipids or phospholipids selected from the group of sterols, sphingolipids and glycerolipids, in particular selected from the group consisting of cholesterol, sphingomyelins, ceramides, phosphatidylcholines, phosphatidylethanolamines, phosphatidylserines, diacylglycerols, and phosphatidic acids containing one or two saturated or unsaturated fatty acids longer than 4 carbon atoms and up to 28 carbon atoms, for the treatment and prevention of bacterial infections.

Particular mixtures considered are mixtures of empty liposomes comprising or consisting of sphingomyelin and cholesterol with other empty liposomes as defined herein, such as mixtures of empty liposomes comprising or consisting of cholesterol and sphingomyelin, with other empty liposomes comprising or consisting of sphingomyelin.

Other particular mixtures considered are mixtures of empty liposomes comprising or consisting of phosphatidylcholine and sphingomyelin with other empty liposomes as defined herein, such as mixtures of empty liposomes comprising or consisting of phosphatidylcholine and sphingomyelin with other empty liposomes comprising or consisting of sphingomyelin.

Other particular mixtures considered are three-component liposome mixtures of empty liposomes comprising or consisting of cholesterol and sphingomyelin with other empty liposomes comprising or consisting of phosphatidylcholine and sphingomyelin, and with empty liposomes consisting of sphingomyelin.

Further particular mixtures considered are four-component liposome mixtures of empty liposomes comprising or consisting of cholesterol and sphingomyelin with other empty liposomes comprising or consisting of phosphatidylcholine and sphingomyelin, with empty liposomes consisting of sphingomyelin, and with empty liposomes comprising or consisting of cholesterol and phosphatidylcholine.

Within the liposomes, the components may be present in different amounts, depending on the tendency to form liposomes, the stability of the liposomes of different composition, and the intended use. Examples are liposomes consisting of two components in approximately 1:1, 2:1, 3:1, 4:1, or 5:1 (weight per weight) composition. Further components may be admixed in approximately 10, 20 or 25% (w/w) amounts.

In the preferred liposomes of the invention cholesterol is present in an amount of 30-70%, preferably 40-60%, e.g. 45-55%, in particular around 50% (w/w), phosphatidylcholine is present in an amount of 10-60%, preferably 20-60%, preferably 40-60%, e.g. 45-55%, more preferably around 50% (w/w); and sphingomyelin is present in an amount of 10-100%, preferably 20-60% or 100%, preferably 40-60%, e.g. 45-55%, more preferably around 50% (w/w) or 100%, the cholesterol:sphingomyelin ratio is between 5:1 and 1:2, preferably 2:1 and 1:2, in particular around 1:1 (w/w), and the cholesterol:phosphatidylcholine or phosphatidylcholine:sphingomyelin ratio is between 5:1 and 1:5, preferably between 2:1 and 1:2, in particular around 1:1 (w/w).

In the liposomal mixtures individual liposome components with different composition are mixed at proportions defined by treatment needs. Examples are approximately 1:1, 2:1, or 3:1 (w/w) for 2-component mixtures; approximately 1:1:1, 2:1:1, or 2:2:1 (w/w) for 3-component mixtures; and approximately 1:1:1:1, 2:1:1:1, 2:2:1:1, or 2:2:2:1 (w/w) for 4-component mixtures.

The liposomes considered consist of one or more phospholipid bilayers. Preferred are large unilamellar vesicles (LUVs) and multilamellar vesicles (MLVs). Most preferred are small unilamellar vesicles (SUVs).

The liposomes are manufactured according to extrusion or sonication or microfluidization (e.g. high pressure homogenization) methods known in the art. For example, the lipids are mixed in an organic solvent such as chloroform. Chloroform is evaporated and the dry lipid film is hydrated in an aqueous solution such as normal saline (0.9% NaCl), Krebs solution, or Tyrode's solution and further sonicated to produce liposomes. If necessary, the size of the liposomes can be controlled by their extrusion through membrane filters of fixed pore diameter. Individually produced liposomes of different lipid compositions are mixed in the required proportions just before application.

Epithelial cells constitute the physical barrier to pathogens. Artificial liposomes are able to protect human embryonic kidney (HEK 293) epithelial cells from streptolysin O (SLO) induced lysis. The SLO pores formed within the plasma membrane are large enough to cause an efflux of cytoplasmic proteins with M, up to 100 kDa. The direct binding of SLO to cholesterol-containing liposomes was confirmed by pre-incubation of the liposomes with the toxin followed by centrifugation. After centrifugation, liposomes, recovered in the pellet, were discarded and the liposome-free supernatants were added to the cells. The supernatants did not inflict any damage on the exposed cells, suggesting that the toxin was efficiently removed from the solution due to its binding to the liposomes.

Figure 1:
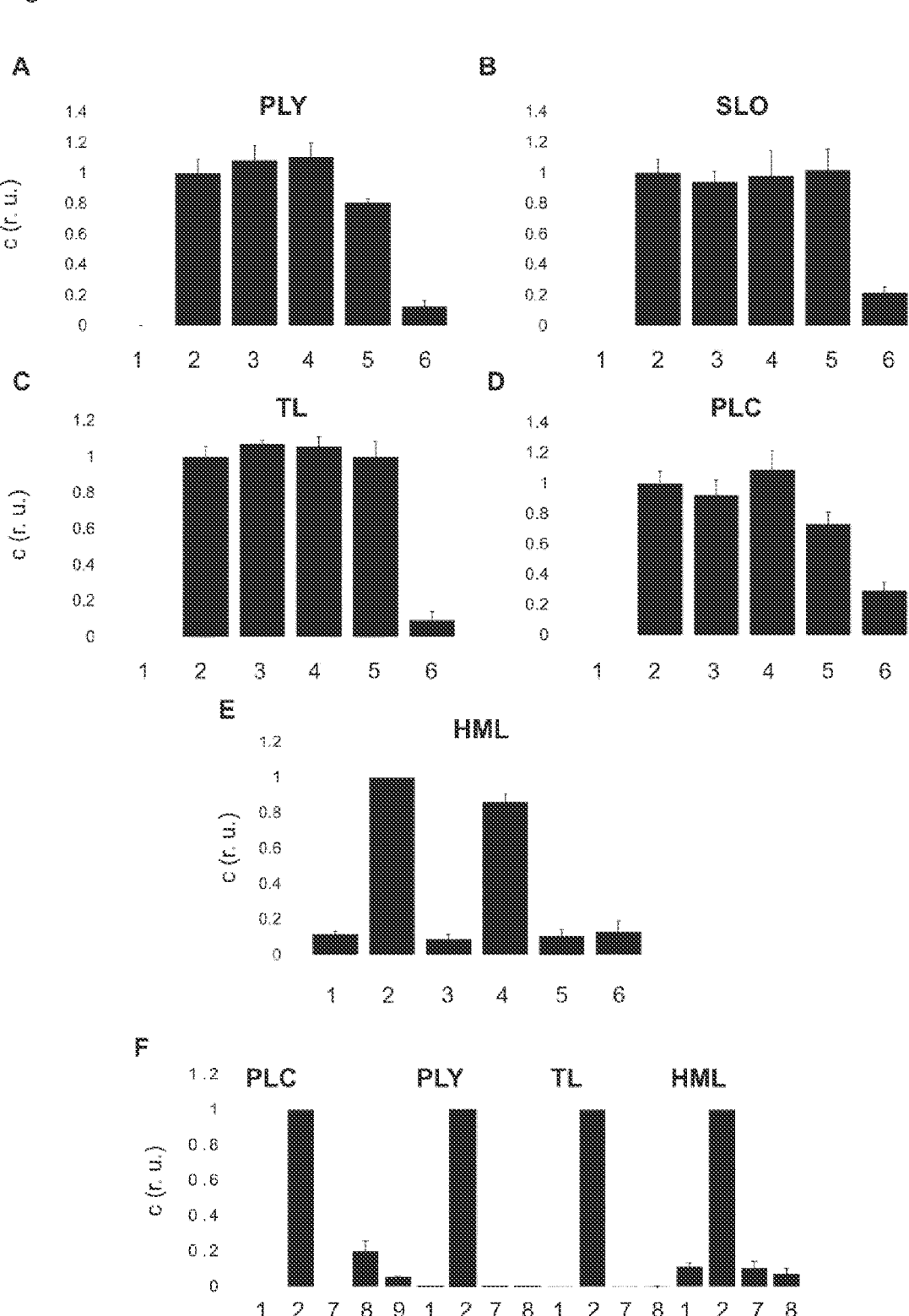
FIG. 1. Liposomes composed of cholesterol and sphingomyelin protect monocytes from cholesterol-dependent cytolysins, α-hemolysin and phospholipase C.

Liposomes protected not only epithelial cells but also cells of the innate immune system against a variety of pore-forming toxins (PFTs). The effects of PFTs on the proliferation of THP-1 human monocytic cell line were assessed in the presence or absence of liposomes of various lipid compositions. Proliferation of THP-1 cells was completely inhibited in the presence of 200 ng of pneumolysin (PLY), 400 ng of streptolysin O (SLO), 200 ng of tetanolysin (TL), 1.2 μg $S. aureus$ α-hemolysin (HML), or 4.5 μg $Clostridium perfringens$ phospholipase C. As shown in FIG. 1 A-D, liposomes containing cholesterol in combination (1:1 w/w) with either phosphatidylcholine (PC), sphingomyelin (Sm) or phosphatidylserine (PS) but not with phosphatidylethanolamine (PE) protected THP-1 cells from cholesterol-dependent cytolysins (PLY, SLO, TL) or phospholipase C (PLC), whereas liposomes, which contained no cholesterol, were ineffective (FIG. 1 F).

In contrast, Ch:PC liposomes (1:1 w/w) and Ch:PS liposomes (1:1 w/w) displayed no protective effect against $S. aureus$ α-hemolysin, which belongs to the group of small pore forming toxins (FIG. 1 E). Liposomes, which contained no cholesterol, were also ineffective (FIG. 1 F). However, liposomes containing Ch:Sm (1:1 w/w) were able to exert a fully protective effect against α-hemolysin (FIG. 1 E). Thus only liposomes composed of cholesterol and sphingomyelin were able to protect THP-1 cells from any of the tested toxins.

FIG. 2 shows that the full protective effect of Ch:Sm (1:1 w/w) liposomes against 200 ng PLY was observed at 3 μg; against 400 ng of SLO at 1.5 μg; against 200 ng TL at 3 μg; against 1.2 μg HML at 25-50 μg, and against 4.5 μg PLC at 100 μg.

FIG. 3 demonstrates that cholesterol in concentrations equal or above 30% (w/w) was required for Ch:Sm liposomes to protect monocytes from PLY, TL or HML. The maximal protection was observed at 50% (w/w) of cholesterol which corresponds to 66 mol % of cholesterol.

Since liposomes composed of cholesterol and sphingomyelin were able to protect cells from either cholesterol-dependent cytolysins or from α-hemolysin, it was investigated whether these liposomes were effective against a combination of both toxin classes. Indeed, 25 μg of Ch:Sm (1:1 w/w) liposomes exerted fully protective effects against the combined action of α-hemolysin (1.2 μg), SLO (400 ng) and TL (200 ng), whereas liposomes composed of Ch:PC (1:1 w/w) had no effect (FIG. 4 A,B). Centrifugation experiments confirm that all three toxins bind directly to Ch:Sm liposomes (FIG. 4 C).

Ch:Sm liposomes are able to protect cultured cells from the entire palette of toxins secreted by clinically relevant strains of bacterial pathogens. The proliferation of THP-1 cells was assessed in the presence of the lytic concentrations of the bacterial culture supernatants and in the presence or absence of liposomes.

As shown in FIG. 5 A,B, Ch:Sm (1:1 w/w) liposomes protected the cells from the effect of toxins secreted by $Streptococcus pyogenes$. The full protective effect against $Streptococcus pyogenes$ toxin(s) was observed at microgram amounts of the liposomes (FIG. 5 C). These amounts are similar to those required for neutralization of lytic concentrations of purified cholesterol-dependent cytolysins, but are much lower than those required for the neutralization of either purified α-hemolysin or purified phospholipase C (FIG. 2) suggesting that cholesterol-dependent cytolysins are solely responsible for the cytolytic action of $Streptococcus pyogenes$.

Ch:Sm liposomes also protected the cells from the effect of toxins secreted by $Streptococcus pneumonia$ (FIG. 6 A-C). Whereas only limited protection was achieved with cholesterol-containing (1:1 w/w) liposomes (FIG. 6 A-C), the mixture of cholesterol-containing (400 μg) and cholesterol-free, Sm-only liposomes (400 μg) was fully protective against this pathogen (FIG. 6 C).

$Staphylococcus aureus$ is notorious for its resistance to the most potent antibiotics. The liposomal toxin-sequestration provides protection even against this pathogen. Ch:Sm (1:1 w/w) liposomes showed only limited protection against toxins secreted by the methicillin-resistant strain of $Staphylococcus aureus$ (MRSA 2040). Similar results were obtained for Ch:PC (1:1 w/w) liposomes: as high as 900 μg of Ch:PC liposomes was required to achieve significant protection, whereas 600 μg of these liposomes showed only slight effect (FIG. 7 A). However, the detailed analysis of different liposomal mixtures demonstrated that addition of as little as 75 μg of sphingomyelin-only liposomes to 600 μg of Ch:PC (1:1 w/w) liposomes achieved full protection against this pathogen (FIG. 7 B). Sm liposomes alone or PC liposomes alone had no protective effect at amounts as high as 900 μg (FIG. 7 B).

The liposomal treatment was also efficient against a clinically relevant 'Doppelhof' strain of $Staphylococcus aureus$, isolated from a septic patient. Neither Ch:Sm (1:1 w/w) nor Ch:PC (1:1 w/w) liposomes nor their combination with Sm-only liposomes were effective when used at concentrations which were protective against MRSA 2040 strain. However, a detailed analysis of the protective action of various liposomal compositions and their combinations demonstrated that—in contrast to MRSA 2040 strain—the cytolytic toxins secreted by the Doppelhof strain were efficiently sequestrated by Sm-only liposomes (FIG. 8 A). Whereas 1200 μg of Sm liposomes alone showed significant protection against the Doppelhof strain, at lower concentrations the mixture containing Sm liposomes and Sm:PC liposomes was more potent than the same amounts of either Sm liposomes or Sm:PC liposomes (FIG. 8 B). The mixture of cholesterol-containing (1:1 w/w; 600 μg) and cholesterol-free, sphingomyelin-only liposomes (1,200 μg) was fully protective against toxins secreted by the $Staphylococcus aureus$ Doppelhof strain (FIG. 8 C).

Thus, not only $Staphylococcus aureus$ or $Streptococcus pneumonia$ secrete multiple cytolytic toxins but also the relative amounts of secreted toxins varies significantly between different strains necessitating the use of complex liposomal mixtures to achieve high-affinity toxin binding for their full neutralization. However, due to non-ideal selectivity of the toxins-liposomes Interactions, significant partial protection can be already achieved with single liposomes, provided their concentration is high enough to promote their low-affinity toxin-binding.

Detailed analysis of different liposomal mixtures demonstrated that 1200 µg (total lipid) of a 1:1:1:1 mixture of Ch:Sm (1:1 w/w) liposomes+Ch:PC (1:1 w/w) liposomes+ Sm-only+Sm:PC (1:1 w/w) liposomes was required for protection against both MRSA 2040 and Doppelhof strains of 'Staphylococcus aureus (FIG. 9). Of importance, owing to the presence of cholesterol-containing liposomes, the 4-component mixture also protects against Streptococcal toxins (see FIGS. 1-5). Thus, the four-component liposomal mixture (1200 µg of total lipid) is able to protect cultured cells from a combined action of Streptococcal and Staphylococcal toxins. The two-component mixture consisting of cholesterol-containing (50% w/w cholesterol) and sphingomyelin-only liposomes was also protective against all bacterial supernatants tested (FIGS. 6-8), however slightly higher amount (1,800 µg of total lipid) of this mixture was required for the full protection against toxins secreted by the Staphylococcus aureus Doppelhof strain (FIG. 8 C).

The bacterial species tested (Streptococcus pneumoniae, Staphylococcus aureus and Streptococcus pyogenes) are known to induce or contribute to the development of life-threatening conditions such as bacteremia. The preferred three- or four-component mixture of liposomes is able to protect laboratory mice from experimentally induced bacteremia or pneumonia.

Mice were injected intravenously with a lethal dose of Staphylococcus aureus Doppelhof strain, a clinical isolate from a septic patient. At 1, 5 and 24 hours following injection of bacteria, mice were injected intravenously either with normal saline (control), with 1 mg/injection of Ch:Sm (1:1 w/w) liposomes, or with 2 mg/injection of a 1:2:2 mixture of Ch:Sm (1:1 w/w) liposomes; Sm-only and Sm:PC (1:1 w/w) liposomes. No control mice survived beyond day 7, with 90% of deaths occurring within 36 hours (FIG. 10 A). Mice treated with cholesterol-sphingomyelin liposomes survived 2-3 days longer than control ones but did not recover after bacteremia. However, treatment with the 3-component liposomal mixture resulted in complete recovery of 6 out of 8 mice.

In the pneumococcal pneumonia model, mice were infected intranasally with the S. pneumoniae strain D39. 30 minutes following injection of bacteria, the mice received a single intranasal injection of 2 mg of a 1:1:1:1 mixture of Ch:Sm (1:1 w/w) liposomes+Ch:PC (1:1 w/w) liposomes+ Sm-only liposomes+Sm:PC (3:1 w/w) liposomes. FIG. 10 B shows that the liposomal mixture provided protection against pneumonia.

In the pneumococcal bacteremia model, mice were injected intravenously with a lethal dose of the S. pneumoniae strain D39. At 8 and 12 hours following injection of bacteria, the mice received intravenously 3 mg/injection of the following liposomes: 1) a 1:1 mixture of Ch:Sm (1:1 w/w) liposomes+Sm-only liposomes; 2) Ch:Sm (1:1 w/w) liposomes; 3) Sm-only liposomes or 4) normal saline. FIG. 10 C shows that no control or Sm-only mice survived beyond 32 hours. However, 6 out of 8 mice that received Ch:Sm+Sm-only liposomal mixture and 3 out of 8 mice that received Ch:Sm liposomes were still alive after 56 hours of bacteremia.

The doses of liposomes (50-150 mg/kg) required for the protection of mice against Staphylococcal bacteremia are known to be non-toxic when used as carriers for intravenous delivery of antibiotics in rats (400 mg/kg; Bakker-Woudenberg I. A. J. M. et al., Antimicrobial Agents and Chemotherapy, 2001, 45:1487-1492). Moreover, the recommended doses of lipid emulsions (e.g "Intralipid", "Lipovenös"), which are infused intravenously in patients suffering from dysfunctions in fatty acid metabolism, contain, in addition to 2.7 g/kg of fatty acids, approximately 300 mg/kg of egg phospholipids; i.e. the phospholipids used in the liposomal preparations of the present invention. Thus, it is safe to administer liposomes for the treatment of bacterial infections in human patients, and liposomes will not elicit adverse events.

The efficiency of liposomal toxin-sequestration can be further improved. Since the liposomes used in this study were mostly multilamellar liposomes and therefore at least half of their lipid content was unavailable for toxin binding, the toxin-sequestrating capacity of unilamellar liposomes is predicted to be at least twice as high. Liposomes composed of selected synthetic lipids, containing uniform acyl chains, and additional lipid species (e.g. ceramide), known to dramatically enhance bilayer lipid de-mixing, provide a better target for bacterial toxins than the liposomes manufactured from natural lipids, which were used in this study. Using PEG-derivatives of phosphatidylethanolamine, the circulation time of liposomes and thus their efficacy can be likewise significantly increased.

The lipid surface (bilayer) of liposomes forms spontaneously in water-based solvents and therefore traps water and other water-soluble inorganic and organic molecules, which might be present during liposome production, inside the liposome. The empty liposomes, used in the present study, are liposomes produced in buffers containing water and simple organic or inorganic molecules (for example NaCl, KCl, $MgCl_2$, glucose, HEPES, and/or $CaCl_2$). However, complex organic molecules (antibiotics, vitamins, adjuvants, and others) can likewise be included during liposome production (loaded liposomes). These complex organic molecules are not expected to interfere with the toxin-sequestrating properties of the liposomes: however they will provide additional therapeutic effects.

The invention further relates to a treatment of bacterial infections comprising administering to a patient in need thereof a therapeutically effective amount of empty liposomes of defined lipid composition or mixtures of empty liposomes of defined lipid composition, as described hereinbefore.

Likewise the invention relates to the prevention of bacterial infections comprising administering to a subject exposed to the risk of infection a preventive amount of empty liposomes of defined lipid composition or mixtures of empty liposomes of defined lipid composition effective for protection.

Bacterial infections considered are infections of the respiratory tract, gastrointestinal tract, urogenital tract, cardiovascular tract, or of the skin, as well as systemic infections caused by bacteria that produce pore-forming toxins and phospholipases, for example caused by Aeromonas hydrophila, Arcanobacterium pyogene, Bacillus thurgiensis, Bacillus anthracis, Bacillus cereus, Clostridium botulinum, Clostridium perfringens, Clostridium septicum, Clostridium sordellii, Clostridium tetani, Corynebacterium diphtheriae, Escherichia coli, Listeria monocytogenes, Pseudomonas aeruginosa, Staphylococcus aureus (including Methicillin-resistant Staphylococcus aureus (MRSA)), Streptococcus pneumonia, Streptococcus pyogenes (also known as Group A Streptococcus (GAS)), Streptococcus equisimilis, Streptococcus agalactiae, Streptococcus suis, Streptococcus intermedius or Vibrio cholera.

Further bacterial infections considered are infections of the nasopharynx system, CNS system, meningeal membranes, vagina, bones (for example osteomyelitis) and joints, kidney, skeletal muscles, outer ear (for example otitis externa), and eye, for example infectious conjunctivitis, bacterial keratitis, and inner-eye infections.

Particular bacterial infections considered as target for a treatment with the liposomes as described above are bacteremia, bacterially infected skin lesions, meningitis, respiratory tract Infections, for example pneumonia, and abdominal infections, such as peritonitis.

Dosages considered for the treatment or prevention of infections are 1 mg to 300 g of liposomes (total lipid) per inhalation/injection/infusion once or several times per day, preferably 100 mg to 10 g once to three times per day. A HED (human equivalent dose) is between 100 and 1000 $mg/m^2$, preferably around 300 $mg/m^2$, or around 8 mg/kg in humans.

Liposomes can be administered as aerosol for the treatment of respiratory tract infections. The preparation of aerosols from liposomes such as the empty liposomes of the invention is known in the art. For example the liquid suspension of liposomes can be delivered with a metered-dose inhaler (MDI), i.e. a device that delivers a specific amount of medication to the airways or lungs, in the form of a short burst of aerosolized medicine that is inhaled by the patient.

For the treatment of bacterial infections of the skin, application of the liposomes of the invention is considered in the form of topical pharmaceutical compositions, such as liquid suspensions and the like. The preparation of a suspension from liposomes such as the empty liposomes of the invention is known in the art. For example, the liposome suspension prepared in normal saline or any other aqueous solution can be applied directly to the skin.

For the treatment of systemic bacterial infections, empty liposomes of the invention are applied in the form of intravenous, intramuscular or subcutaneous injections. Injection solutions are prepared by standard methods known in the art, for example as suspensions of the liposomes in sterile normal saline. Such suspensions can be directly injected. It is also considered to apply the liposomes of the invention in a formulation useful for sublingual or buccal application. For the treatment of peritonitis, intraperitoneal application is considered. Eye drops may be used for bacterial infection of the eyes.

The empty liposomes of the invention will sequestrate bacterial toxins and thus prevent bacteria from penetrating the host's epithelia or their systemic propagation. The development of systemic disease can thus be averted or slowed; and the pathogens can be efficiently cleared by cells of the host's innate immune system, which are likewise protected from toxins by the liposomes.

The liposomes themselves are not cytotoxic, nor are they bactericidal. Therefore, it is unlikely that they will exert selective antibacterial pressure, which would further the emergence of drug-resistant bacteria. The empty liposomes of the invention mimic structures that already exist in the host's cells, in order to bait bacterial toxins. Therefore it is inconceivable that bacteria will adapt to the liposomal challenge: every attempt to escape the bait by decreasing the affinity of their toxins to the liposomes inevitably leads to the emergence of toxins which are likewise ineffective against the host's cells.

Liposome-based chemotherapy is an appealing alternative to both antibiotic therapy and to a treatment with toxin-sequestrating antibodies.

The invention also relates to a treatment of bacterial infections comprising administering to a patient in need thereof a therapeutically effective amount of empty liposomes before, after, together or in parallel with a standard antibiotic treatment of the bacterial infection.

In combination with antibiotic treatment, apart from neutralization of actively secreted bacterial toxins during the active phase of an infection, the liposomal treatment will provide additional benefits for a patient by sequestrating the toxins which are released during antibiotic treatment by lysed bacteria, a condition which is known to be detrimental, for example, during meningitis, in *Streptococcus pneumonia* infection (acute pneumolysin release) and *Streptococcus pyogenes* infection (acute release of streptolysin O).

In this combination treatment the empty liposomes and liposome mixtures may be considered as adjuvants, and the corresponding method of treatment as adjunct treatment.

A limitation for liposomal therapy is its restricted efficiency in immunocompromised individuals since the clearance of bacteria lies not with the chemotherapeutic agent but with the host's own immune system. However, even in immunodeficient patients, liposomal treatment in combination with bactericidal chemotherapy will be beneficial: slowing down the development of systemic disease, and thus will provide the organism with the much needed time to allow antibiotics to unfold their full bactericidal potential.

Antibiotic treatment considered together with the treatment using empty liposomes according to the invention is, for example, treatment with cephalosporins and other β-lactam antibiotics, glycopeptides, lincosamides, lipopeptides, macrolides, penicillins and penicillin combinations, quinolones, sulfonamides, chloramphenicol and chloramphenicol analogues, tetracyclines, clindamycin, and folate inhibitors, as listed above. Particular antibiotics considered in a treatment together with empty liposomes of the invention are carbapenems such as imipenem, cilastin and meropenem. $2^{nd}$ generation cephalosporins such as cefuroxime, $3^{rd}$ generation cephalosporins such as ceftazidime and ceftriaxone, $4^{th}$ generation cephalosporins such as cefepime, glycopeptides such as vancomycin, macrolides such as clarithromycin, penicillins such as amoxicillin and flucloxacyllin, penicillin combinations such as amoxicillin/clavulanate and piperacillin/tazobactam combinations, and quinolones such as ciprofloxacin and moxifloxacin, and fluoroquinolones such as levofloxacin and gemifloxacin.

All components of the empty liposomes of the invention are substances, which occur naturally in humans. These liposomes are therefore well tolerated and cleared from the body via physiological pathways. Liposome aerosols should be used for the prevention of pneumonia and other diseases of the respiratory tract by the general population during seasonal Influenza epidemics. Most importantly, prophylactic measures based on liposome aerosols or other liposome applications will be helpful in the prophylaxis of MRSA pneumonia or bacteremia in hospitals, *Pseudomonas aeruginosa, S. aureus* or *S. pneumonia* infections, and in other settings, which favor the spread of infectious diseases.

EXAMPLES

Toxins

Streptolysin O (SLO) from *Streptococcus pyogenes, a*-hemolysin from *Staphylococcus aureus*, tetanolysin (TL) from *Clostridium tetani* and phospholipase C from *Clostridium perfringens* were purchased from Sigma. Pneumolysin was obtained from Prof. Kadioglu (Cruse G. et al., J. Immunol. 2012; 184:7108-7115). Other toxins include Panton-Valentine leukocidin (PVL) from *S. aureus*, listeriolysin O (LLO) from *Listeria monocytogenes*, perfringolysin O (PFO) from *Clostridium perfringens*, suilysin (SLY) from *S. suis*, intermedilysin (ILY) from *S. intermedius*, cereolysin O (CLO) from *B. cereus*, thuringiolysin O (TLO) from *B. thuringiensis*, botulinolysin (BLY) from *C. botulinum*, sordellllysin (SDL) from *C. sordelli*, pyolysin (PLO) from *Arcanobacterium pyogenes*. Culture supernatants from *Streptococcus pneumoniae, Streptococcus pyogenes* and *Staphylococcus aureus* were obtained from Profs. K. Mühlemann (Bern) and E. Gulbins (Essen).

or to 66 mol % cholesterol. The amounts of liposomes are given as the amount of total lipids used for their preparation.

In an alternative method, about 25 ml of each formulation was made by the ethanol hydration and extrusion method. The final formulations were sterile filtered and filled in autoclave serum glass vials (final concentration: 40 mg/ml). The liposome particle sizes are in the range of 80-150 nm with good PDI (polydispersity index). The results for the osmolality measurement are also included. They are all in the range of around 400 mmol/kg which is pretty close to the desired physiological level.

TABLE 1

| | | | | | | | |
|---|---|---|---|---|---|---|---|
| | Specifications | | | | | | |
| Liposomes | Mean diameter (nm) | Half-width (nm) | Poly-dispersity index | Zeta potential (mV) | SD (mV) | Osmolality (mmol/kg) | pH |
| Ch:Sm | 130 | 46 | 0.13 | −1.40 | 0.6 | 371 | 7.02 |
| Sm | 81 | 31 | 0.15 | −3.35 | 0.5 | 346 | 7.02 |
| Ch:Sm:PEG2 % | 116 | 37 | 0.11 | −9.83 | 0.7 | 401 | 7.03 |
| Ch:Sm:PEG5 % | 122 | 43 | 0.12 | −15.70 | 0.5 | 392 | 7.04 |
| Sm:PEG2 % | 96 | 42 | 0.19 | −9.5 | 0.5 | 398 | 7.02 |
| Sm:PEG5 % | 111 | 45 | 0.17 | −15.10 | 0.5 | 387 | 7.02 |

Cell Culture

The human embryonic kidney cell line (HEK 293) was maintained as described by Monastyrskaya K et al., Cell Calcium. 2007, 41:207-219. The human acute monocytic leukemia cell line (THP-1) was maintained in RPMI 1640 medium containing 10% FBS, 2 mM L-glutamine and 100 U/ml penicillin, 100 μg/ml streptomycin.

Transfections

CFP (cyan-fluorescent protein) was transiently expressed in HEK 293 cells (Monastyrskaya et al., loc. cit.). CFP-expressing HEK 293 cells were used for laser scanning module (LSM) imaging experiments 2 days after transfection.

Liposomes

Cholesterol (Ch) (C-8667), Sphingomyelin (Sm) from chicken egg yolk (S0756), phosphatidylcholine (PC) from soybean (P7443), phosphatidylethanolamine (PE) from bovine brain (P9137) and phosphatidylserine (PS) sodium salt from bovine brain (P5660) were purchased from Sigma. The lipids were individually dissolved in chloroform at 1 mg/ml concentrations and stored at −20° C. For the preparation of liposomes the chloroform solutions of individual lipids were mixed in the composition and the proportions, which are given in the text, to produce routinely 50-500 μl of the final solution. Chloroform was completely evaporated for 20-50 min at 60° C. 50 μl or 100 μl of Tyrode's buffer (140 mM NaCl, 5 mM KCl, 1 mM MgCl₂, 10 mM glucose, 10 mM HEPES; pH=7.4) containing 2.5 mM CaCl₂ was added to the tubes containing films of dried lipids and vigorously vortexed. The lipid suspensions were incubated for 20-30 min at 45° C. in an Eppendorf thermomixer with vigorous shaking. To produce liposomes, the final lipid suspensions were sonicated 3×5 sec at 6° C. in a Bandelin Sonopuls sonicator at 70% power. The liposomal preparations were left for at least 1 hour at 6° C. before they were used in experiments. The concentration of individual lipids in the liposomes is always given as the weight per weight (w/w) ratio. In liposomes containing cholesterol and sphingomyelin, the 1:1 (w/w) ratio corresponds to 50%/6 (w/w)

Toxin-Induced Cell Lysis and Protective Effects of Liposomes

In human embryonic kidney epithelial cells (HEK 293), toxin-induced lysis was monitored as a decline of cytoplasmic fluorescence due to a pore-induced efflux of intracellular CFP. Confluent HEK 293 cells seeded on 15 mm glass coverslips (2.5×10⁵ cells per coverslip) were mounted in a perfusion chamber at 25° C. in Tyrode's buffer containing 2.5 mM CaCl₂) and their fluorescence was recorded in an Axiovert 200 M microscope with a laser scanning module LSM 510 META (Zeiss, Germany) using a ×63 oil immersion lens (Monastyrskaya et al., loc. cit.). At time-point=0, the buffer was replaced by 100 μl or 200 μl of the same buffer containing additionally a cytolytic quantity of a given toxin (e.g. 120 ng of SLO from *Streptococcus pyogenes*) and 20 mM/L dithiothreitol (DTT). To investigate the protective effect of liposomes on toxin-induced cell lysis, at time-point=0, cells were routinely challenged with 100 μl of a mixture containing toxin/DTT and liposomes of various concentrations and of various lipid composition. The toxin-liposome mixture was prepared immediately before addition to the cells (with 20 to 30 sec of handling delay). In some cases, 100 μl of solution containing liposomes alone was added first to the cells followed (with 20 to 30 sec of handling delay) by 100 μl of toxin-containing solution. The protective effects of the liposomes were similar under either experimental condition. The images were analyzed using the "Physiology evaluation" software package (Zeiss, Germany).

The effects of purified PFTs or bacterial culture supernatants on the proliferation of a human monocyte cell line (THP-1) were assessed in the presence or absence of liposomes of various lipid compositions. Routinely, 100-600 μl of toxin-containing solution (Ca²⁺-Tyrode's buffer or BHI broth) was added to 100 μl (5×10⁴ cells) of cells maintained in culture medium and pre-mixed with 50-150 μl of liposomes of various lipid-composition. After incubation for 3 hours, 1-2 ml of fresh culture medium was added to the tubes. The cells were counted each day or every second day for 8-12 days. The toxins and the liposomes were present for the whole duration of an experiment. The data presented in the diagrams correspond to day 5 or day 6, when the cell growth was still in the linear phase.

Comparison of "Empty" and "Filled" Liposomes

The protection against culture supernatants of *S. aureus* or *S. pneumoniae* by the mixture of "empty" Ch:Sm+Sm-only liposomes is compared with that of mixture of Ch:Sm+Sm-only liposomes filled with a fluorescent dye such as Fluorescein, Oregon Green 488, Rhodamine, or Texas Red.

The protection against culture supernatants of *S. aureus* or *S. pneumoniae* by the mixture of "empty" Ch:PC liposomes is compared with that of mixture of Ch:PC liposomes filled with fluorescent dye such as Fluorescein, Oregon Green 488, Rhodamine, or Texas Red.

Protection by Lipid-Coated Surfaces

Beads coated by cholesterol and sphingomyelin are tested for their toxin-sequestering activity against culture supernatants of *S. aureus* or *S. pneumoniae*.

In Vivo Effect in Combination with Antibiotic Treatment on Bacteremia Induced by *S. aureus* or *S. pneumoniae*.

The 2-component mixture of Ch:Sm and Sm-only liposomes; 3-component mixture of Ch:Sm; Sm-only and Sm:PC (1:2:2) liposomes and of a 4-component mixture of Ch:Sm, Sm-only, Sm:PC and Ch:PC (1:1:1:1) are tested in a mouse models of bacteremia Induced by either a penicillin-susceptible strain *Streptococcus pneumonia* or by Methicillin-resistant *Staphylococcus aureus* (MSSA). Two types of MSSA strains are considered, characterized by their ability to secrete or not the toxin Panton-Valentine leukocidin (PVL). In addition, 2-component mixture of Ch:Sm and Sm-only pegylated liposomes (2% PEG or 5% PEG) are also tested.

Laboratory mice are inoculated by intraperitoneal (i.p.), intravenous (i.v.) or intranasal (i.n.) injection of approximately $10^7$ or $10^8$ cfu/ml of bacteria.

For each bacteria strain, each infection route, and for each liposome mixture (LP mixture), Intravenous Injections of two different doses (2 mg/kg or 6 mg/kg) of the LP mixture is started either six hours (t=6), twelve hours (t=12), eighteen hours (t=18), or twenty four hours (t=24) after the bacterial challenge (in each case, the injection of LP mixture is followed by either one additional injection 12 hours, or two additional injections 4 hours and 24 hours after the initial injection), with or without penicillin treatment (30 mg/kg).

Antibiotic treatment is initiated at the same time of liposome treatment. Two types of controls were performed: infection without treatment and infection treated with antibiotic alone (at t=6, t=12, t=18, or t=24).

For each bacteria strain and for each liposome mixture, and for each dose of liposome and each route of infection, there were 10 groups of animals.

| Group | |
|---|---|
| 1 | No treatment (control) |
| 2 | Penicillin alone |
| 3 | LP mixture at t = 6 |
| 4 | LP mixture at t = 6 + penicillin |
| 5 | LP mixture at t = 12 |
| 6 | LP mixture at t = 12 + penicillin |
| 7 | LP mixture at t = 18 |
| 8 | LP mixture at t = 18 + penicillin |
| 9 | LP mixture at t = 24 |
| 10 | LP mixture at t = 24 + penicillin |

In group 1, the survival of 50% of the group were followed for at least 8 days, 25% of the group were euthanized one hour after the bacterial challenge and the remaining 25% 6 h after the bacterial challenge.

Bacterial counts were determined in blood and several organs such as lung, spleen, and kidney.

Read out: survival, signs of infections, metabolism (serial measurements of weight loss and recovery, 02 consumption and $CO_2$ production rates measured by indirect calorimetry, resting energy expenditure (REE) calculated with the modified Weir formula); inflammation cytokines profile (ELISA was performed on serum for tumor necrosis factor (TNF)-alpha, macrophage inflammatory protein (MIP)-2, and IL-1b).

Minimal Bactericidal Concentration (MBC)

No activity of sphingomyelin/cholesterol liposomes against usual strains:

| Strain | MBC (mg/mL) |
|---|---|
| ATCC 27853 *P. aeruginosa* | >16 |
| *S. aureus* | >16 |
| 762 | >16 |

The testing of the minimum bactericidal concentration (MBC) was carried out following the guidelines proposed by the Clinical and Laboratory Standards Institute (CLSI).

For the broth microliter dilution tests, 96-well plates supplemented with 50 μL of 0.5-16 mg/mL liposomes were inoculated with 50 μL of Mueller Hinton broth containing a bacterial cell suspension of $1-5\times10^5$ colony-forming units (CFU) per mL of *S. aureus*. The plates were incubated for 24 h at 36° C. MBC was determined by transferring 10 μL aliquots from the wells broth microtitre dilution plates onto Columbia blood agar (Oxoid, Wesel, Germany). The inoculated plates were further incubated for 24 h at 36° C. and then colonies were counted.

The invention claimed is:

1. A method of treating a bacterial infection in a patient in need thereof comprising intravenously administering to the patient a therapeutically effective amount of a mixture comprising:
   (i) empty liposomes composed of sphingomyelin and 30% (w/w) or more cholesterol, wherein the empty liposomes do not encapsulate an antibiotic or other drug, and
   (ii) other empty liposomes composed of sphingomyelin, wherein the other empty liposomes do not encapsulate an antibiotic or other drug;
   and wherein said mixture does not comprise liposomes that encapsulate an antibiotic or other drug.

2. The method of claim 1, wherein some or all of the liposomes are modified with polyethylene glycol.

3. The method of claim 1, wherein the bacterial infection is bacteremia, a bacterially infected skin lesion, meningitis, or a respiratory tract infection.

4. The method of claim 1, wherein said therapeutically effective amount of said mixture is administered before, after, together, or in parallel with an antibiotic medication against the bacterial infection.

5. The method of claim 1, wherein said mixture is administered before, after, together or in parallel with a further pharmaceutically active compound.

6. The method of claim 5, wherein said further pharmaceutically active compound comprises at least one of an antibiotic, an anti-inflammatory drug, a vasopressor, a vasoconstrictor, a pain killer, or an anti-toxin.

7. The method of claim 1, wherein the empty liposomes (i) are composed of sphingomyelin and 40%-70% (w/w) cholesterol.

8. The method of claim 1, wherein the empty liposomes (i) are composed of sphingomyelin and 40%-66% (w/w) cholesterol.

9. The method of claim 1, wherein the empty liposomes (i) are composed of sphingomyelin and 40%-60% (w/w) cholesterol.

10. The method of claim 1, wherein the empty liposomes (i) are composed of sphingomyelin and 45%-55% (w/w) cholesterol.

11. The method of claim 1, wherein the empty liposomes (i) are composed of sphingomyelin and 50% (w/w) cholesterol.

12. The method of claim 1, wherein the mixture is about a 1:1 (w/w) mixture of the empty liposomes (i) and the other empty liposomes (ii).

* * * * *